US012622868B2

(12) United States Patent
Bhamla et al.

(10) Patent No.: US 12,622,868 B2
(45) Date of Patent: May 12, 2026

(54) DEVICES, SYSTEMS, AND METHODS FOR FACILITATING TISSUE DELIVERY OF DRUG

(71) Applicant: Georgia Tech Research Corporation, Atlanta, GA (US)

(72) Inventors: Mohammed Saad Bhamla, Atlanta, GA (US); Gaurav Byagathvalli, Cumming, GA (US); Dengning Xia, Shanghai (CN); Mark R. Prausnitz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 760 days.

(21) Appl. No.: 17/924,803

(22) PCT Filed: May 28, 2021

(86) PCT No.: PCT/US2021/034959
§ 371 (c)(1),
(2) Date: Nov. 11, 2022

(87) PCT Pub. No.: WO2021/243270
PCT Pub. Date: Dec. 2, 2021

(65) Prior Publication Data
US 2023/0190640 A1 Jun. 22, 2023

Related U.S. Application Data

(60) Provisional application No. 63/031,767, filed on May 29, 2020.

(51) Int. Cl.
*A61M 37/00* (2006.01)
*A61K 9/00* (2006.01)
(Continued)

(52) U.S. Cl.
CPC ............ *A61K 9/0021* (2013.01); *A61K 39/12* (2013.01); *A61M 37/0015* (2013.01);
(Continued)

(58) Field of Classification Search
CPC ........ A61K 9/0021; A61M 2037/0023; A61M 37/0015; A61N 1/0476; A61N 1/327; A61N 1/36017
See application file for complete search history.

(56) References Cited

U.S. PATENT DOCUMENTS 5,658,247 A * 8/1997 Henley .................... A61N 1/30
604/20
7,285,113 B2 10/2007 Yeshurun
(Continued)

FOREIGN PATENT DOCUMENTS

CN 104307098 A 1/2015
JP 3135390 U 9/2007
(Continued)

OTHER PUBLICATIONS

Broderick et al. (2011) Piezoelectric permeabilization of mammalian dermal tissue for in vivo DNA delivery leads to enhanced protein expression and increased immunogenicity, Human Vaccines, 7:sup1, 22-28.
(Continued)

*Primary Examiner* — Deanna K Hall
(74) *Attorney, Agent, or Firm* — Eversheds Sutherland (US) LLP

(57) ABSTRACT

Devices and methods are provided for administering a drug to a biological tissue in a patient, such as by intracellular and/or dermal delivery. The device includes a piezoelectric pulse generator; and an array of microneedle electrodes electrically coupled to the piezoelectric pulse generator, wherein the device, following insertion of the microneedle
(Continued)

electrodes into the biological tissue, is configured to generate and deliver one or more electrical pulses through the microneedle electrodes effective to electroporate cells in the biological tissue and enable delivery of a drug into the electroporated cells.

30 Claims, 14 Drawing Sheets

(51) Int. Cl.
　　*A61K 39/12*　　　　(2006.01)
　　*A61N 1/04*　　　　(2006.01)

(52) U.S. Cl.
　　CPC ......... *A61N 1/0424* (2013.01); *A61N 1/0476* (2013.01); *A61M 2037/0023* (2013.01)

(56) References Cited

U.S. PATENT DOCUMENTS

| | | | |
|---|---|---|---|
| 7,315,758 | B2 | 1/2008 | Kwiatkowski et al. |
| 8,386,005 | B2 | 2/2013 | Schouenborg |
| 10,940,301 | B2 | 3/2021 | McAllister et al. |
| 2003/0092182 | A1 | 5/2003 | Sakamoto et al. |
| 2007/0106207 | A1 | 5/2007 | Withey |
| 2007/0276318 | A1* | 11/2007 | Henley .................. A61N 1/303 604/20 |
| 2009/0030364 | A1 | 1/2009 | Harmon et al. |
| 2009/0326441 | A1 | 12/2009 | Iliescu et al. |
| 2011/0295100 | A1 | 12/2011 | Hegde et al. |
| 2012/0046598 | A1 | 2/2012 | Kardos et al. |
| 2013/0306356 | A1 | 11/2013 | Allen et al. |
| 2019/0167983 | A1 | 6/2019 | Kardo et al. |

FOREIGN PATENT DOCUMENTS

| | | |
|---|---|---|
| JP | 2010253199 A | 11/2010 |
| WO | 1999029364 A1 | 6/1999 |
| WO | 2000044438 A1 | 8/2000 |
| WO | 2017058793 A1 | 4/2017 |

OTHER PUBLICATIONS

International Search Report from PCT/US2021/034959 dated Sep. 23, 2021.
Extended European Search Report for European Application No. 21813010.2 dated Mar. 12, 2024.
Byagathvalli et al., "ElectroPen: An ultra-low-cost, electricity-free, portable electroporator", PLoS Biol, 2020: 18(1), pp. e3000589.

* cited by examiner

DEVICES, SYSTEMS, AND METHODS FOR FACILITATING TISSUE DELIVERY OF DRUG

CROSS REFERENCE TO RELATED APPLICATIONS

This application claims benefit of U.S. Provisional Application No. 63/031,767, filed May 29, 2020, which is incorporated herein by reference.

STATEMENT REGARDING FEDERALLY SPONSORED RESEARCH OR DEVELOPMENT

This invention was made with government support under grant number R01AI143844 awarded by the National Institutes of Health. The U.S. government has certain rights in this invention.

BACKGROUND

This invention is generally in the field of devices and methods for the administration of therapeutic and prophylactic agents to persons in need thereof, and more particularly to methods and devices for the introducing therapeutics, vaccines, nucleic acids, and the like into biological tissues and/or across tissue barriers, especially when the site of drug action is located within cells.

Numerous formulations and devices have been investigated for delivery of drugs, nucleic acids, biologicals such as vaccines and therapeutic proteins through the skin and into cells. The stratum corneum of mammalian skin is an effective barrier, particularly for molecules larger than 500 Daltons, even when using penetration enhancers, ultrasound, electroporation or microneedles. Conventional devices using ultrasound and electroporation usually require costly technology, and in all cases require access to a continuous source of electric power such as AC power outlets or batteries.

The plasma membrane is another effective barrier, particularly for molecules that are not normally taken up by active transport processes, even when nanoparticle, lipid, polymer and other formulations are used. This is especially important for drugs based on genetic material, such as DNA and RNA. The site of action of a DNA-based drug is typically within the cell nucleus. The site of action of a RNA-based drug is typically within the cell cytosol.

A critical need therefore remains for an inexpensive device for dermal and intracellular drug delivery, which does not require adjunctive technology such as ultrasound generators and a continuous source of electric power such as AC power outlets or batteries, and which does not require chemical formulations that can have adverse side effects.

BRIEF SUMMARY

Electroporation-based drug delivery devices and methods are provided, which may overcome one or more of the foregoing problems associated with conventional devices and methods for administration of drugs to patients.

In one aspect, a device is provided for use in administering a drug into or across a biological tissue in a patient. In embodiments, the device includes (i) a piezoelectric pulse generator; and (ii) an array of microneedle electrodes electrically coupled to the piezoelectric pulse generator, wherein the device, following insertion of the microneedle electrodes into the biological tissue, is configured to generate and deliver one or more electrical pulses, produced by the piezoelectric pulse generator, through the microneedle electrodes effective to electroporate cells in the biological tissue and enable delivery of a drug into the electroporated cells. In some embodiments, the device includes the drug and is configured to release the drug to the biological tissue. In some other embodiments, the drug is not provided as part of the device, and the drug is administered to the biological tissue from a separate source. The drug may be a therapeutic or prophylactic molecule larger than 500 Daltons, such as those including nucleic acids. In some embodiments, the drug is a vaccine, such as an RNA vaccine.

In another aspect, a method is provided for delivering a drug into or across a biological tissue. In embodiments, the method includes (i) positioning the device, which includes an array of microneedle electrodes electrically coupled to a piezoelectric pulse generator, adjacent to a target tissue site in a biological tissue; (ii) inserting the microneedle electrodes into the target tissue site; (iii) activating the device to deliver one or more electrical pulses through the microneedle electrodes and into the target tissue site effective to electroporate cells at the target tissue site; (iv) and delivering the drug into tissues of the target tissue site. In some embodiments, the biological tissue is mammalian skin or a mucosal membrane. In some embodiments, the target tissue site comprises the dermis or epidermis. In some embodiments, the drug is administered to the target tissue site before, or contemporaneously with, delivery of the electrical pulse. In some embodiments, the drug is administered to the target tissue site from or through the microneedle electrodes. In some other embodiments, the drug is administered to the biological tissue from another part of the device or from a separate source.

BRIEF DESCRIPTION OF THE DRAWINGS

FIGS. 11C and 11D are reprehensive profiles after pulsing with a commercial benchtop electroporator of voltage and current, respectively.

DETAILED DESCRIPTION

Figure 1A:
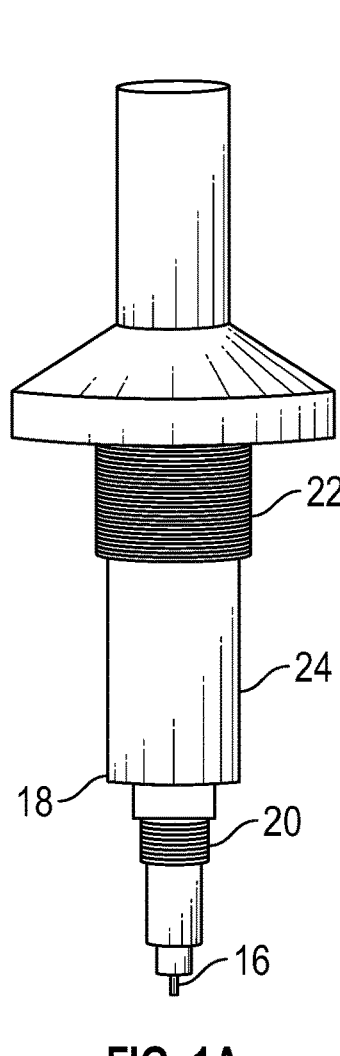
FIG. 1A is a plan view of a housing and piezoelectric pulse generator of a drug delivery system, according to one embodiment of the present disclosure

A new and improved electroporation device and methods of administration of drug to a patient have been developed. The methods and devices are particularly useful for delivery of drugs larger than 500 Da, such as those comprising nucleic acids or other biologicals.

As used herein, the term "peak voltage" refers to the maximum voltage drop achieved across the electrodes when applied to biological tissue; the term "peak-to-peak voltage" refers to the voltage difference between the peak positive voltage and the peak negative voltage when applied to biological tissue; the term "peak static voltage" refers to the maximum voltage drop achieved across the electrodes when the electrodes are directly applied to the leads of an oscilloscope; the term "peak-to-peak static voltage" refers to the voltage difference between the peak positive voltage and the peak negative voltage when electrodes are directly applied to the leads of an oscilloscope; the term "peak current" refers to the maximum current through the biological tissue; the term "nominal electric field strength" refers to the voltage across the electrodes divided by the spacing between oppositely charged electrodes; the term "initial pulse length" refer to the time between the initiation of the pulse and the time when the voltage first returns to the voltage before initiation of the pulse when applied to biological tissue; and the term "total pulse length" refers to the time between the initiation of the pulse and the time when the voltage no longer achieves an absolute value greater than 10% of the absolute value of the peak voltage when applied to biological tissue.

The Devices and Methods

The device includes a piezoelectric pulse generator; and an array of microneedle electrodes electrically coupled to the piezoelectric pulse generator, wherein the device, following insertion of the microneedle electrodes into the biological tissue, is configured to generate and deliver an electrical pulse through the microneedle electrodes effective to electroporate cells in the biological tissue and enable delivery of a drug into the electroporated cells. In a preferred embodiment, the device is sized and shaped to be handheld and manually operable, preferably with the same hand. In some embodiments, the device further includes a base from which the array of microneedle electrodes extend. The base and array of electrodes may be part of a cartridge configured to be releasably coupled to a housing that contains the piezoelectric pulse generator.

In some embodiments, the device further includes the drug to be administered, and includes any suitable means for storing and releasing the drug to the biological tissue site. In some embodiments, the drug is in the form of a coating on the microneedle electrodes. In some embodiments, the drug is stored in one or more reservoirs in the device, for example, in the cartridge, and/or at least a portion of the microneedle electrodes each include a hollow bore, and conduits in fluid communication with the one or more reservoir, such that the hollow bores of the microneedle electrodes provide for passage of the drug from the reservoirs and into the biological tissues before, following or at the same time as insertion of the microneedle electrodes into the biological tissue. In another variation, the cartridge body includes apertures adjacent to the microneedle electrodes, which may be solid, i.e., without a hollow bore, wherein the apertures are in fluid communication with the reservoirs and provide release of the drug from the reservoirs through the apertures at the interface of the biological tissue and the cartridge body, whereby the drug may flow into punctures created by the microneedle electrodes. In another embodiment, the microneedles may have grooves or other nonplanar surface features that provide a pathway for fluid flow along the microneedle surface (i.e., as opposed to a hollow bore enabling fluid flow in the interior of the microneedle), thereby facilitating drug delivery into the biological tissue.

In some embodiments, the drug is provided separately from the device. For example, the device may be administered to a target tissue site of the biological tissue by a conventional means such a hypodermic needle, jet injection, iontophoresis, or a separate microneedle device. The microneedles for administering the drug may be part of the electroporate device or may be a separate device.

In embodiments, the methods provided herein for delivering a drug into or across a biological tissue include (i) positioning the electroporator device at a target tissue site in a biological tissue; inserting the microneedle electrodes into the target tissue site; and (ii) activating the device to deliver the one or more electrical pulses through the microneedle electrodes and into the target tissue site effective to electroporate cells at the target tissue site; and (iii) delivering the drug into tissues of the target tissue site. The drug may be administered to the target tissue site before delivery of the electrical pulse, after delivery of the electrical pulse, contemporaneously with delivery of the electrical pulse, or some combination thereof. The drug may be administered to the target tissue site from or through the microneedle electrodes, or from a separate delivery means.

The methods may include manually applying a force to the electroporator device effective to penetrate the tissue surface with the array of microneedle electrodes, and then manually pressing a button or switch on the device that triggers a mechanical force onto a piezoelectric thereby to produce an electric pulse effective to induce pore formation in cells. Depressing the same button or switch, or a different button or switch, may actuate drug release, e.g., from an on-board reservoir.

In a preferred embodiment, the electroporator device has no stored electrical energy (e.g., it has no battery) and has no wired or wireless attachment to an energy source (e.g., it is not plugged into an electrical outlet). The energy that generates the voltage across the electrodes of the device is provided by mechanical action of the user of the device. For example, the energy associated with manually pressing a button or switch on the device provides the energy that generated the voltage across the electrodes. A piezoelectric component may transduce the mechanical energy input by the user into electrical energy that generates the voltage.

Advantageously, the devices and methods provide an ultra-low-cost (<2 USD, such as less than ~1 USD), hand-held, battery-free electroporation system that is inexpensive enough for single-use and robust enough for repeated use if desired. In some embodiments, a system or kit is provided which consists of the device and blister packs of drug/microneedle electrode array cartridges. In addition, the present devices are easily portable and suitable for handheld operation. For example, the devices may weigh under 300 g, preferably under 150 g, preferably under 100 grams, preferably under 50 grams), may have a size less than 100 cm$^3$, preferably less than 50 cm$^3$, and preferably less than 20 cm$^3$, and require no battery or power sources beyond the piezoelectric crystal, which in turn may be powered by a mechanical input by the user.

The device and methods can be applied to any suitable biological tissues of the patient. That is, the electrical pulse and drug may be delivered to cells that are at or near a physically accessible part of the body of a patient. The patient may be a human or other mammal. The delivery of electrical pulses and drug may be to cells in the skin, cells in epithelial layers of the body, or cells in the body's interior that are accessible for example laparoscopically or due to a surgical intervention. In some embodiments, the biological tissue comprises mammalian skin. In some preferred embodiments, the target tissue site comprises the dermis or epidermis. In some other embodiments, the biological tissue comprises a mucosal membrane. In some embodiments, the target tissue site may be in the mouth, nose, eye, gastrointestinal tract, or vagina.

In particular methods, the methods advantageously use the microneedle electrodes to target delivery to the skin, which has been shown to provide greater immunogenicity for DNA, RNA, and other vaccines compared to vaccines delivered into muscle. The microneedles are short, in some embodiments, may be just 650 μm long, which can concentrate the electric field in the epidermis, as well as possibly the dermis. The epidermis is especially rich in antigen-presenting cells and is thus a desirable location for delivery. In addition, delivery to the epidermis beneficially keeps electric fields away from stimulating sensory and motor nerves deeper in the dermis, subcutaneous or muscle tissue below.

The devices and methods can be used to administer any suitable drug, particularly one where electroporation may facilitate cellular uptake of the drug. The drug may be essentially any therapeutic or prophylactic agent known in the art or developed. In embodiments, the drug is a small molecule, a biologic, or a vaccine. Non-limiting examples include therapeutic proteins (such as antibodies, enzymes, growth factors, hormones, interferons, interleukins, engineered proteins, and vaccines), RNA (such as messenger RNA (mRNA), RNA interference (RNAi) including short interfering RNA (siRNA) and micro RNA (miRNA), anti-sense RNA (asRNA) or short hairpin RNA (shRNA) or RNA aptamers), DNA (such as plasmids, oligonucleotides, DNA aptamers, DNAzymes), anti-cancer drugs, antibacterial drugs, inhibitors (of, for example, protein synthesis, cell wall synthesis, enzymatic activity, biochemical pathways), drugs affect intracellular or intercellular signaling, drugs affecting gene regulation. The devices and methods may be used to deliver two or more different drugs. In a preferred embodiment, the drug comprises a nucleic acid. In a preferred embodiment, the drug is a vaccine. In various embodiments, the drug is an RNA or DNA vaccine, such as a mRNA vaccine. The vaccine may be one selected to be effective against any of a variety of viruses, bacteria or other pathogens, including but not limited to SARS-CoV-2, Ebola, influenza, etc. The vaccine may be comprised of mRNA and/or DNA encoding one or more antigens, or be a vaccine effective against multiple variants of a disease.

As noted above, the device includes a piezoelectric pulse generator; and an array of microneedle electrodes electrically coupled to the piezoelectric pulse generator. The piezoelectric pulse generator and coupled array of microneedle electrodes are sometimes referred to herein as an "ePatch" device or an electroporation device. The array of microneedle electrodes is sometime referred to herein as a "Microneedle Electrode Array" or MEA. The piezoelectric pulse generator may include any mechanism effective to generate a suitable electrical pulse from a piezoelectric crystal. In some embodiments, the piezoelectric pulse generator includes (i) a piezoelectric crystal, (ii) a spring-latch hammer mechanism configured to strike a surface of the piezoelectric crystal effective to generate the electrical pulse, and (iii) electrical connections for conducting the electrical pulse to the microneedle electrodes.

The device may include any suitable piezoelectric crystal. In some embodiments, the piezoelectric crystal comprises lead zirconate titanate (PZT). It may include various dopants known in the art. In some embodiments, the piezoelectric crystal includes lead zirconate titanate, silicon nitride, barium titanate, quartz, zinc oxide, and/or sodium tungstate. The piezoelectric crystal is a material which exhibits a piezoelectric effect of large magnitude, that is the production of an electric field and thereby a large voltage output with a short time constant in the form of a pulse. This may occur through a mechanical force, pressure, or compression exerted against the crystal's surface, creating a temporary deformation resulting in the formation of electric charges which are then released as an electrical pulse.

The device may include a casing for the piezoelectric crystal, which includes electrical connections for relaying the pulse to the microneedle electrodes. The casing may include a lower electrode and a side electrode, which extends from the casing. The device may include a cartridge that contains the array of microneedle electrodes and includes a first receptacle for mating engagement with the lower electrode and a second receptacle for mating engagement with the side electrode, the first and second receptacles being in electrical communication with the microneedle electrodes.

The device may include a toggle switch with a wedge controlling latch configured to release a hammer driven by decompression of a spring. A pin, such as a metal pin, may be disposed between the hammer and the piezoelectric crystal. The device in one embodiment may operate as follows: After the microneedle electrodes are inserted into the skin, mucosa, or other biological tissue, a user exerts a force against a toggle switch, such as a thumb-toggle switch, which compresses a lower spring, and pushes a wedge towards the hammer locked in a latch. When the user pushes all the way, the wedge forces the hammer out of the latch which subsequently strikes a pin sitting against the crystal to concentrate the force. The voltage output may then be directed to electrodes on the device. An upper spring may then be decompressed to reset the hammer and latch into the original locked state. The user may repeat the operation to generate additional pulses as needed to provide an effective electroporation of the tissues for delivery of the drug into the cells.

The microneedle electrodes are sized, shaped, and spaced in the array in a manner effective to penetrate into the target tissues (e.g., through the stratum corneum) and to achieve electroporation of cells with the electrical pulses generated by the piezoelectric crystal. The microneedles are mechanically robust to prevent shearing off, or otherwise damaging, the microneedle electrodes during microneedle insertion or withdrawal. The microneedle electrodes may be made of a stainless steel, nickel, iron, or other metals or alloys, or other suitably electrically conductive biocompatible material. The microneedle electrodes may include a straight or tapered body, which may be cylindrical or square shaped, and may include a tapered tip portion. The microneedle electrodes may be manufactured using any suitable method known in the art, for example lithographic etching technology, 3D printing, micromolding, and laser cutting. The microneedle electrodes may be solid, have a hollow bore extending from a base to the tip or may have one or more grooves in the sides of the microneedles.

In some embodiments, the microneedle electrodes extend from a series of metal plates which are configured to conduct the electrical pulses from the piezoelectric pulse generator to the microneedle electrodes. In some embodiments, a linear array of the microneedle electrodes extends from one side of each of the metal plates. It is understood that on a plate, some of the microneedle electrodes may be positive and some may be negative. All of the microneedles electrodes on a plate may not be connected to each other. The connections may be selective among the electrodes, and there can be multiple connections/electrode groupings. In some embodiments, the plates are parallel to each other and spaced apart from one another. In some embodiment the plates are fixed in an insulating holder, for example one made of a polymeric material. For example, the insulating holder may be a cartridge body having a series of slots into which the plates may be fixed with the microneedle electrodes extending from a surface of the cartridge body.

In some embodiments, two or more microneedles with the same polarity (i.e., cathodes or anodes) are part of the same piece of electrically conducting materials (e.g., metal), for example formed from a single piece of material and cut, etched or otherwise processes to achieve the microneedle array geometry. The material could be a sheet and the microneedles could be in the same plane as the sheet, or they could be at a non-zero angle, such as about 90 degrees, from the plane of the sheet.

In some embodiments, the microneedles electrodes may comprise a non-electrically conductive microneedle array with conductive material (e.g., metal) patterned on the surface of the microneedle array in such a way that all of the anodes are electrically connected and all of the cathodes are electrically connected, but the anodes and cathodes and electrically isolated from each other on the microneedle array.

In some embodiments, the microneedle electrodes are made of conductive material and are connected to a substrate that is not conductive (i.e., the microneedle electrodes and the substrate comprise the microneedle array). Microneedle electrodes are electrically connected to each other by patterning conductive material on one or more of the surfaces of the substrate and/or by electrical connections located in parts of the ePatch other than the microneedle array, which may involve wires electrically connected to microneedle electrodes via the microneedle array surface and/or through holes in the substrate.

In some embodiments the microneedle electrodes of the same polarity are all connected to each other electrically on the microneedle array or in other cases the microneedle electrodes are not all connected to each other electrically on the microneedle array, but are connected to each other through electrical connections not on the microneedle array but located elsewhere in the ePatch device.

In some embodiments, the array of microneedle electrodes is made by a method as described in S O Choi, Y C Kim, J W Lee, J H Park, M R Prausnitz, M G Allen "Intracellular protein delivery and gene transfection by electroporation using a microneedle electrode array," *Small,* 8:1081-1091 (2012), which is incorporated herein by reference.

In some embodiments, the array of microneedle electrodes is arranged to be inserted into a tissue area from 1 mm$^2$ to 10 cm$^2$.

The array of microneedle electrodes can have any suitable number of microneedle electrodes. In some embodiments, the array has from 2 to 10,000 microneedle electrodes, such as from 50 to 5000, from 100 to 1000, or from 20 to 200 microneedle electrodes. Other numbers of microneedles per array in a device are envisioned. The microneedle electrodes may be arranged in various patterns. Cathodes and anodes may be in alternating rows, may be in a checkerboard pattern or may be arranged in other patterns.

In some embodiments, the microneedle electrodes have a length from 10 μm to 2 mm. In some embodiments, the microneedle electrodes have a length between 50 μm and 1.5 mm, or between 100 μm to 1 mm. In some preferred embodiments, the length is within the range of 10 μm to 1 mm, such as in the range of 650 μm or 750 μm. In some embodiments, the microneedles may have a base width or diameter from 50 μm to 600 μm. Other microneedle electrode dimensions are envisioned.

In some embodiments, the cartridge of the array of microneedle electrodes is configured to be replaceable and disposable, and the piezoelectric pulse generator is configured to be reusable with a series of such cartridges.

The electroporation portion of the devices described herein provide an electrical pulse capable of increasing delivery of molecules into cells. The use of piezoelectric crystals as the source of the electric pulses induces membrane permeabilization through a high-voltage, short time-constant pulse (e.g., microseconds), which is believed to induce a temporary change in the cell membranes of cells in the electric field produced by the microneedle electrodes during an electric pulse, which includes cells in contact with, or in the vicinity of the microneedle electrode, allowing molecules to enter the cells, and produce the intended effect.

In some preferred embodiments, the piezoelectric pulse generator produces bipolar, oscillatory pulses, which may electroporate cells more effectively compared to conventional monopolar or exponential-decay or square-wave pulses.

Closely spaced microneedle electrodes are needed to achieve the high field strength required for microsecond pulses to work effectively for electroporation of the cells in biological tissues. Because the piezoelectric pulses are of microseconds duration, effective electroporation benefits from a field strength>500 V/cm. To achieve such a high field strength, the microneedle electrodes need to be spaced suitably close, for example, less than 1 mm from each other, i.e., from nearest neighboring electrodes in the array. This tight spacing allows piezoelectric pulses of hundreds of volts to achieve the very large required field strengths. In contrast, much larger voltages would be needed to achieve this field strength if conventional clamp electrodes with spacing of many millimeters or centimeters were used In some embodiments, the microneedle electrodes arrays of the present devices and methods have a spacing in the array between 0.1 mm and 10 mm, preferably between 0.2 mm and 5 mm, and more preferably between 0.3 mm and 2 mm. In some embodiments, the spacing is in the range from 0.5 mm to 1.5 mm.

Conventional electroporators generate millisecond pulses. In contrast, the present devices and methods typically generate shorter pulses on the order of microseconds, for example less than 100 µs, such as about 10 µs. As the pulse length gets shorter, the electric field needs be higher. Larger voltages and shorter spacing between electrodes allows for larger electric field strength. Conventional electroporators use long, moderate-voltage pulses; however, these can frequently cause burning and/or tattooing. The short duration pulses of systems in the present disclosure provide the added advantage of an enhanced safety profile. The field strength may not be constant as a function of position in the microneedle array. However, generally the field strength can be determined using voltage divided by the electrode spacing. Thus, electric fields sufficient to electroporate tissue may be generated using only microsecond pulses when the electrode spacing is small, as described herein.

In some embodiments, the device is configured to produce a nominal electric field strength between 100 V/cm and 30,000 V/cm, preferably between 200 V/cm and 10,000 V/cm, and more preferably between 300 V/cm and 5,000 V/cm. For example, the nominal electric field strength may be in the range from 500 V/cm to 3,500 V/cm.

In some embodiments, the one or more electrical pulses have a peak voltage absolute value between 10 V and 10,000 V, preferably between 50 V and 5,000 V, and more preferably between 100 V and 1,000 V. For example, the peak voltage absolute value may be in the range from 200 V to 500 V. In some embodiments, the one or more electrical pulses have a peak static voltage absolute value between 100 V and 35,000 V, preferably between 1,000 V and 30,000 V. For example in the range of 15,000 V to 27,500 V.

In some embodiments, the one or more electrical pulses have a peak-to-peak voltage absolute value between 20 V and 20,000 V, preferably between 100 V and 10,000 V, and more preferably between 200 V and 2,000 V. For example, the peak-to-peak voltage absolute value may be in the range from 400 V to 1,000 V. In some embodiments, the one or more electrical pulses have a peak-to-peak static voltage absolute value between 200 V and 70,000 V, preferably between 2,000 V and 60,000 V, and more preferably between 25,000 V and 50,000 V.

In some embodiments, the one or more electrical pulses have a ratio of the absolute value of the peak voltage to the absolute value of the peak-to-peak voltage between 0.1 and 10, preferably between 0.3 and 5, and more preferably between 0.5 and 2.

In some embodiments, the one or more electrical pulses have a ratio of the absolute value of peak static voltage to the absolute value of the peak voltage which is greater than 2, or greater than 5, or greater than 10, or greater than 100.

In some embodiments, the one or more electrical pulses have a peak current absolute value between 1 A and 1,000 A, more preferably between 5 A and 500 A, and more preferably between 10 A and 100 A. For example, the peak current absolute value may be in the range from 20 A to 50 A.

In some embodiments, the one or more electrical pulses each have an initial pulse length between 1 µs and 1,000 µs, preferably between 3 µs and 100 µs, and more preferably between 5 µs and 50 µs. For example, the initial pulse length may be in the range from 10 µs to 30 µs.

In some embodiments, the one or more electrical pulses each have a total pulse length between 5 µs and 5,000 µs, preferably between 10 µs and 1,000 µs, and more preferably between 20 µs and 500 µs. For example, the total pulse length may be in the range from 30 µs to 200 µs.

In some embodiments, the one or more electrical pulses each have a ratio of the initial pulse length to the total pulse length between 1.5 and 100, preferably between 2 and 50, and more preferably between 3 and 20.

The foregoing pulse values refer to pulses in biological tissues, such as the skin, unless they are identified as static voltages (i.e., peak static voltage, peak-to-peak static voltage). It is noted that similar, conventional piezoelectric devices are designed to make sparks in air. In contrast, the piezoelectric devices described herein are coupled with microneedle electrodes and used to pass current through a conductive medium (i.e., no sparks).

In preferred embodiments of the present devices and methods, a bipolar oscillating pulse is used for electroporation instead of a monopolar pulse, often in the form of an exponential-decay or square wave pulse which is conventionally used for electroporation. This bipolar oscillating pulse may be a natural result of the compression and extension of piezoelectric crystals induced by a spring shock in the case containing the piezoelectric crystal. Compared to conventional monopolar pulses, bipolar oscillating pulses are not only able to produce a dielectric breakdown of the cell membrane but can also produce a sonicating motion in the cell membrane, inducing more effective cell poration. Furthermore, oscillating pulses may provide better cell viability by avoiding polarizing the cell membrane beyond the critical potential for an extensive period, therefore, preventing irreversible rupture of the cell membrane.

Figures 7A, 7B:
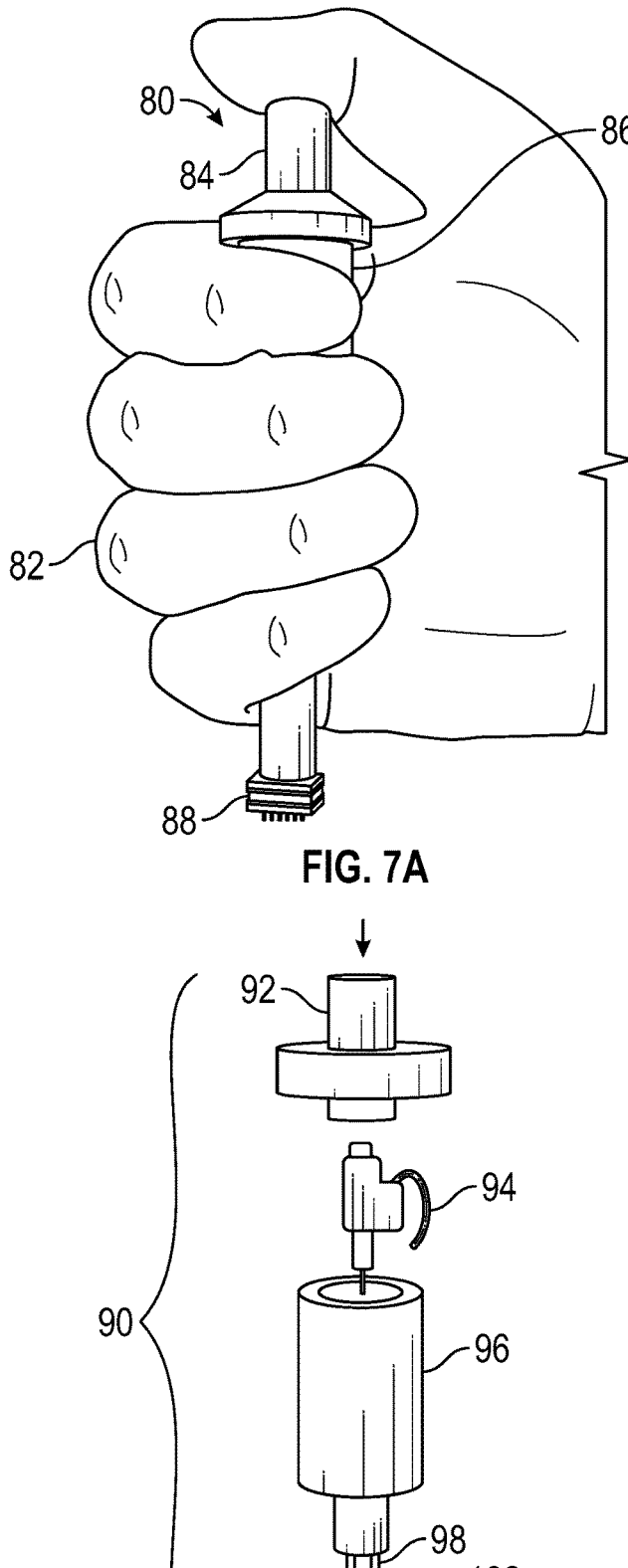
FIGS. 7A-7F are schematics of an electroporator according to one embodiment of the present disclosure.

One embodiment of the electroporation device is depicted in FIGS. 7A-7B. The system includes a hand toggle, a piezoelectric crystal, a case surrounding the crystal, copper wires, and an MEA.

In embodiments, the microneedle electrodes are arranged on the base in a square or rectangular arrangement, with the rows or columns functioning alternatively as positive and negative electrodes. Alternatively, the positive and negative electrodes may be in a checkerboard pattern. In embodiments, a cartridge comprises the array of microneedles. Other arrangements, such as circular arrangements, are possible; the microneedles can be arranged in any suitable shape.

In one embodiment, the MEA has an array of 54 microneedle electrodes measuring 650 µm long with 0.9 mm spacing between rows of oppositely charged electrodes that localize the electric field to the epidermis. Electroporation requires strong electric fields on the order of $10^3$ V/cm, with shorter pulses requiring larger field strengths. This means that more-closely spaced electrodes can electroporate with lower voltages. Close electrode spacing also decreases electric field penetration depth into the skin, which facilitates epidermal targeting and reduces nerve stimulation.

The pulse length (or decay constant) is on the order of microseconds (e.g., 1-1000 microseconds), and possibly nanoseconds (e.g., 1-1000 nanoseconds), depending on the piezoelectric crystal utilized. The pulse length can be manipulated, for example, through choosing different dopants utilized in the crystal manufacturing process, choosing different dopants, different piezoelectric materials, and other methods known in the art. The pulse length may be in the range of 1 ns to 1 ms, preferably in the range from 1 to 100 μs.

While for non-oscillatory pulses, the initial and total pulse lengths are the same, the pulses of the devices and methods described herein may be oscillatory, such that the initial and total pulse lengths may not be the same. Moreover, while conventional electroporators generate substantially monopolar pulses, the devices and methods described herein preferably use bipolar pulses, wherein each pulse alternates between positive and negative.

Figure 1B:
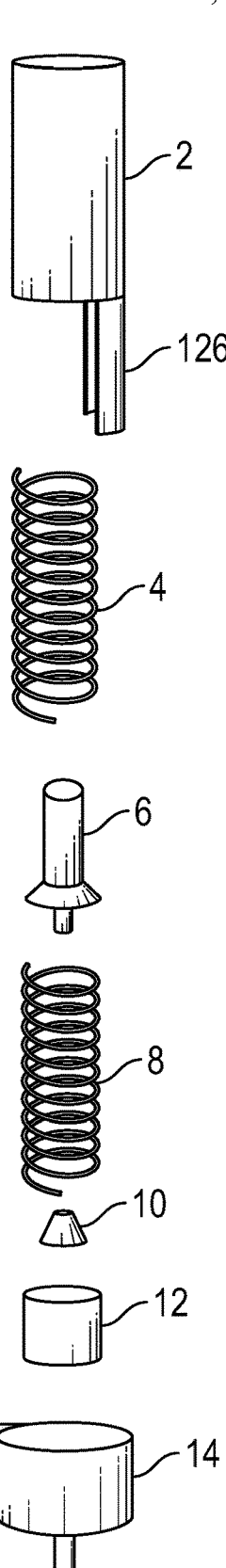
FIG. 1B is an exploded view of a piezoelectric pulse generator, according to one embodiment of the present disclosure.

FIGS. 1A-1B depict one example of a housing and piezoelectric pulse generator of the electroporation devices described herein. Here, a user toggle switch 2 may be compressed, thereby compressing an upper spring 4 bringing the spring 4 closer to a hammer 6. When the toggle switch 2 is pushed all the way in, the attached wedge 126 pushes the hammer 6 out of its latch and the upper spring 4 decompresses. As the toggle switch 2 is pressed, this spring 4 is also compressed storing elastic potential energy. Once the wedge 126 pushes the hammer 6 out of its latch, this spring 4 decompresses to project the hammer 6. The hammer 6, which may made of metallic material, is projected onto the metal pin 10 which is in contact with the piezoelectric crystal 12 to induce the mechanic deformation and produce an electrical pulse. As the toggle switch 2 is compressed, this spring 8 (the lower compression spring) is also compressed below and around the hammer 6. After the latch-release phase when the hammer 6 is projected onto the metal pin 10 and thereby the crystal 12, this spring 8 is decompressed restoring the toggle switch 2, hammer 6, and upper compression spring 4. This pin 10 rests on top of the piezoelectric crystal 12 and comes into contact with the hammer 6 after it is projected. The metal pin 10 concentrates the force onto the crystal 12. The crystal 12 generates the electrical pulse when struck by the hammer 6 onto the metal pin 10. The device also comprises a crystal casing 14 with electrode contacts. This casing 14 houses the piezoelectric crystal 12 and has a pin extending from the bottom forming the first electrical connection 16 and also has a conductive piece extending to the second electrical connection on the side 18. A metal piece protruding from the crystal casing 14 serving as an electrical connection, here the lower electrical connection 16. A metal piece protruding from the side mechanism casing 24 also serves as an electrode, here the side electrode 18. Threads may be used to screw optional casing on top. Both lower threads 20 and upper threads 22 may be used. The spring-latch-hammer mechanism casing 24 that houses elements of the mechanism. A wedge piece 126 is attached to the toggle switch 2 is used to push the hammer 6 out of the latch and project onto the metal pin 10 and crystal 12.

Figure 2B:
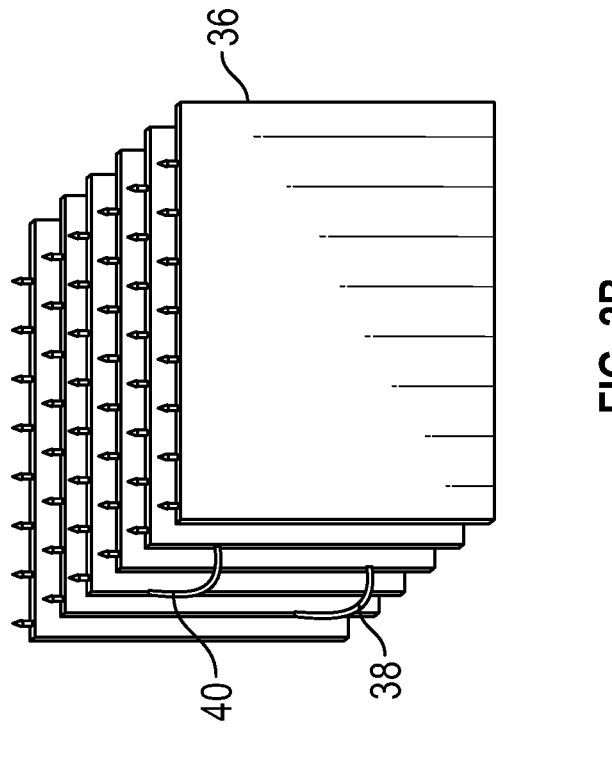
FIGS. 2A and 2B are perspective views of an array of microneedle electrodes and their associated metal plates within (FIG. 2A) or without (FIG. 2B) a cartridge casing therefor, according to embodiments of the present disclosure.
Figure 2A:
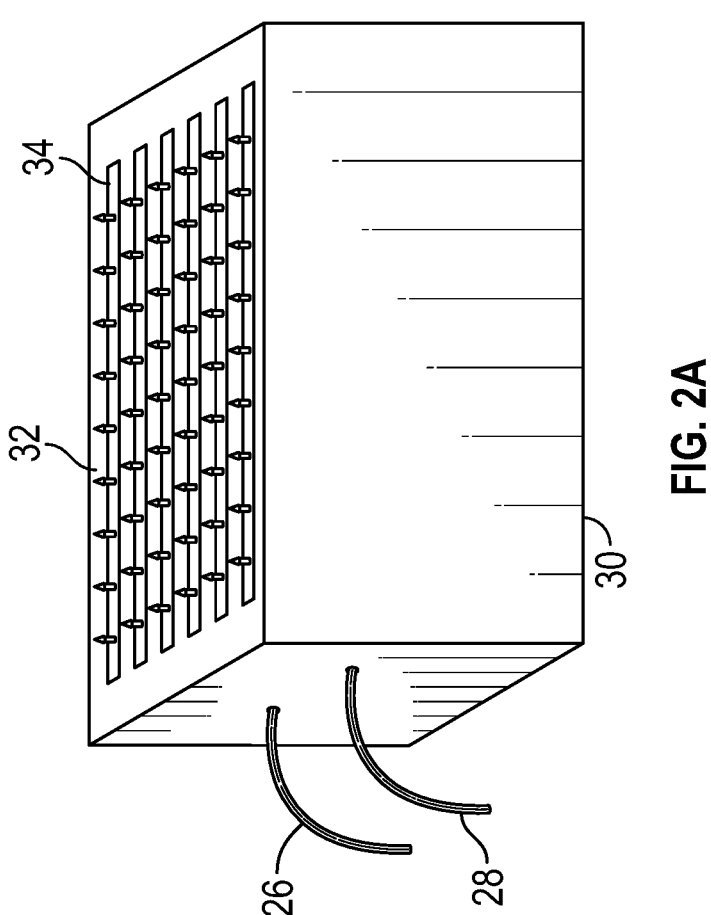

FIGS. 2A-2B depict one embodiment of a microneedle-electrode array and holder or cartridge therefor. FIG. 2A show a microneedle-electrode casing (the cartridge casing) 30 which serves as a housing for a series of six metal plates 36, shown in both FIG. 2A and FIG. 2B, which have a linear array of microneedle electrodes extending from one edge surface 34 of the plates 36 that is adjacent to the surface 32 of the casing 30. Wire terminals 26, 28 are connected directly or indirectly to the metal plates 36 within the casing and extend from the casing 30 for connecting to the piezo pulse generator. The first wire 38 and second wire 40 connect the metal conducting plates 36 to transmit the electrical pulse from the piezo pulse generator to the microneedle electrodes. The wires 38, 40 may serve, for example, as positive and negative electrical connections, respectively.

Figure 3:
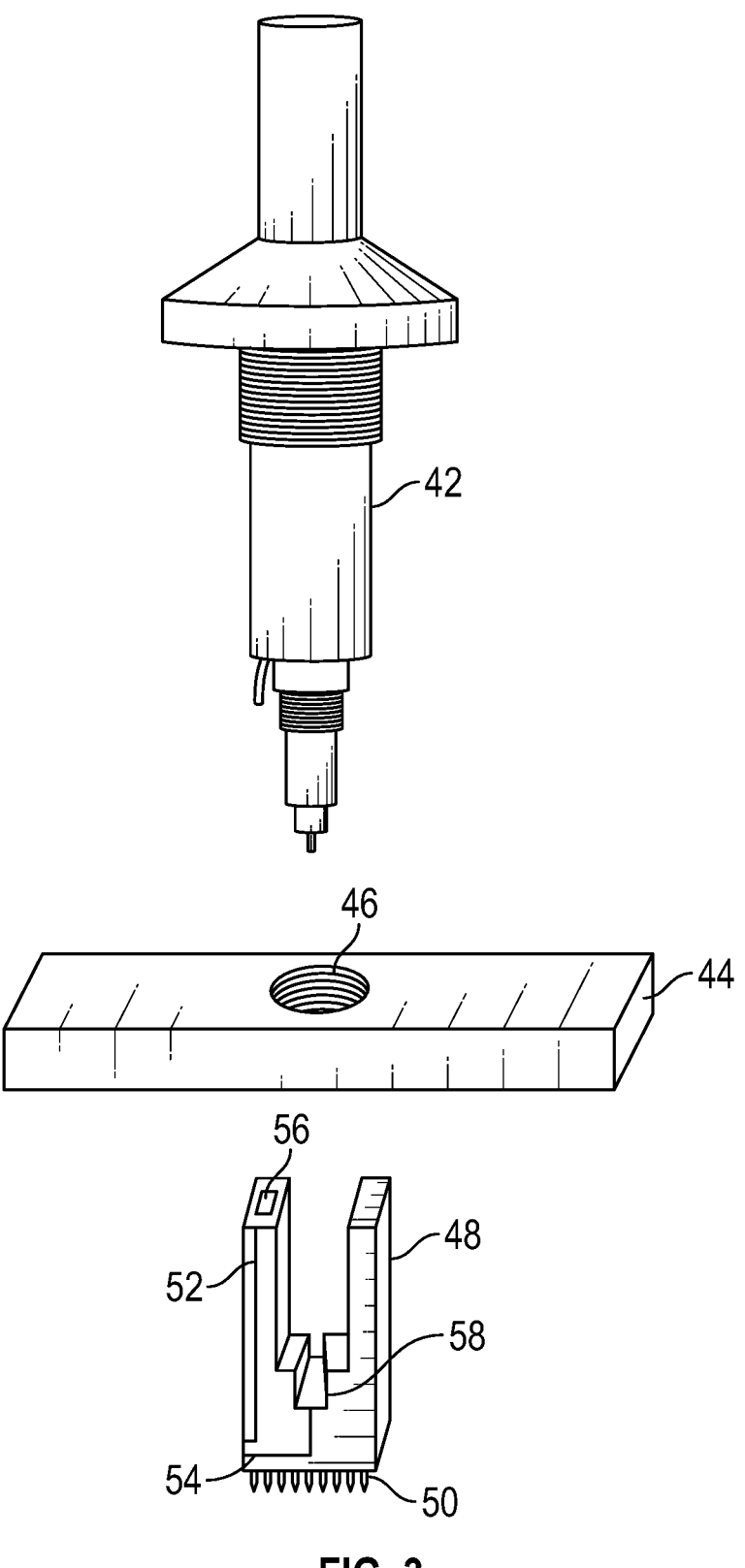
FIG. 3 is a perspective view of a drug delivery system comprising (i) a housing containing a piezoelectric pulse generator, and (ii) a cartridge which comprise an array of microneedle electrodes, according to an embodiment of the present disclosure.

FIG. 3 depicts one embodiment of the device that includes (i) a housing containing a piezoelectric pulse generator, and (ii) a cartridge which comprise an array of microneedle electrodes. The piezo pulse generator 42 may be like the one shown in FIGS. 1A-1B. As shown in FIG. 3, the device further includes an array of microneedle electrodes 50 extending from a cartridge 48. The cartridge includes electrode insertion points 56 and 58, depicted here as slots, to mate with electrical connections from the piezo pulse generator 42 to electrically connect with the metal conductors 52, 54, which in turn are electrically connected to the microneedle electrodes 50. The device may further include an optional support handle 44, which may aid the user in depressing a toggle switch on the piezo pulse generator 42. The support handle 44 may include a threaded aperture 46 to mate with threads on the housing of the piezo pulse generator 42.

Figure 4:
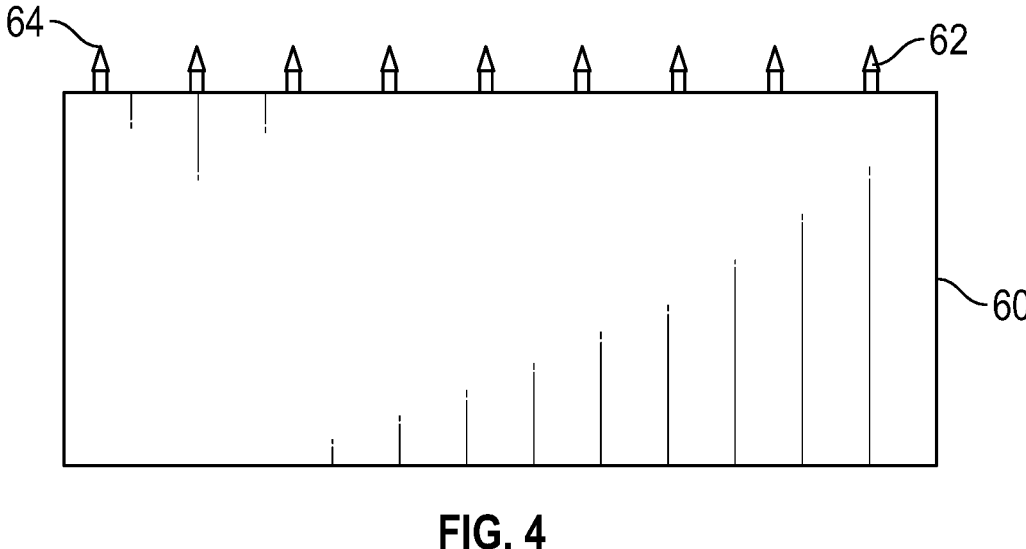
FIG. 4 is a schematic of a cartridge having an array of solid microneedle electrodes, according to one embodiment of the present disclosure.
Figure 5:
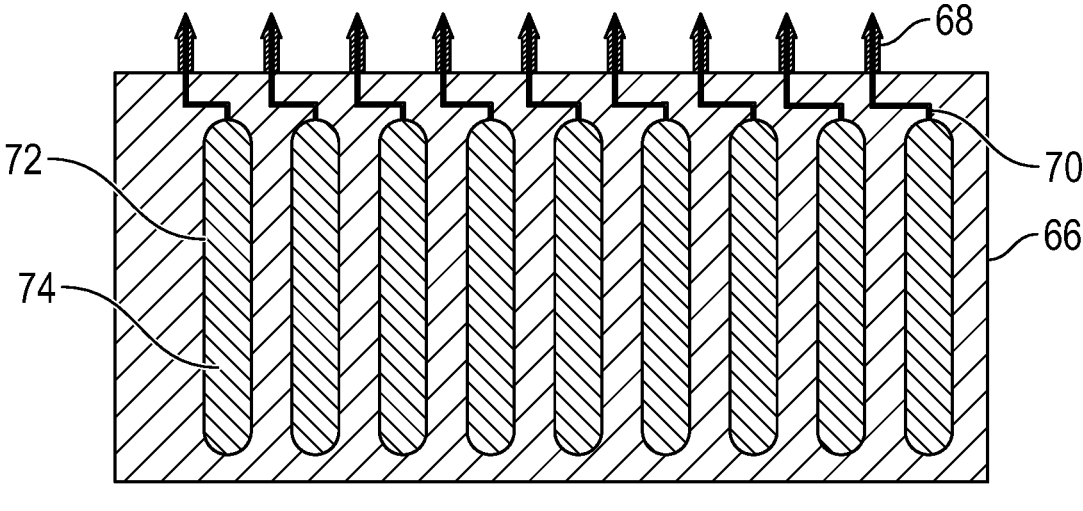
FIG. 5 is a schematic of a cartridge having an array of hollow microneedle electrodes, according to another embodiment of the present disclosure.

FIGS. 4-5 show two embodiments of microneedle electrode arrays and casings/cartridges. As shown in FIG. 4, an end portion of the device, e.g., a cartridge, includes an array of solid microneedle electrodes 62. The microneedles 62 are connected to/contained within a casing 60. Here, the drug 64 is coated on the surface of one or more of the microneedle electrodes 62. As shown in FIG. 5, an end portion of the device 66 e.g., a cartridge, includes an array of hollow microneedle electrodes 68 and a plurality of reservoirs 72 containing a fluid drug formulation 74. In other embodiments (not shown), the cartridge may have a single, shared reservoir supplying drug to the hollow microneedle electrodes. Conduits 70 provide fluid communication between the reservoirs 72 and the bores of the hollow microneedle electrodes 68. The reservoirs 74 are useful for storing the fluid drug formulation 74 prior to release and may include more drug than can be contained in a coating on solid microneedles.

Figures 6A, 6B, 6C, 6D:
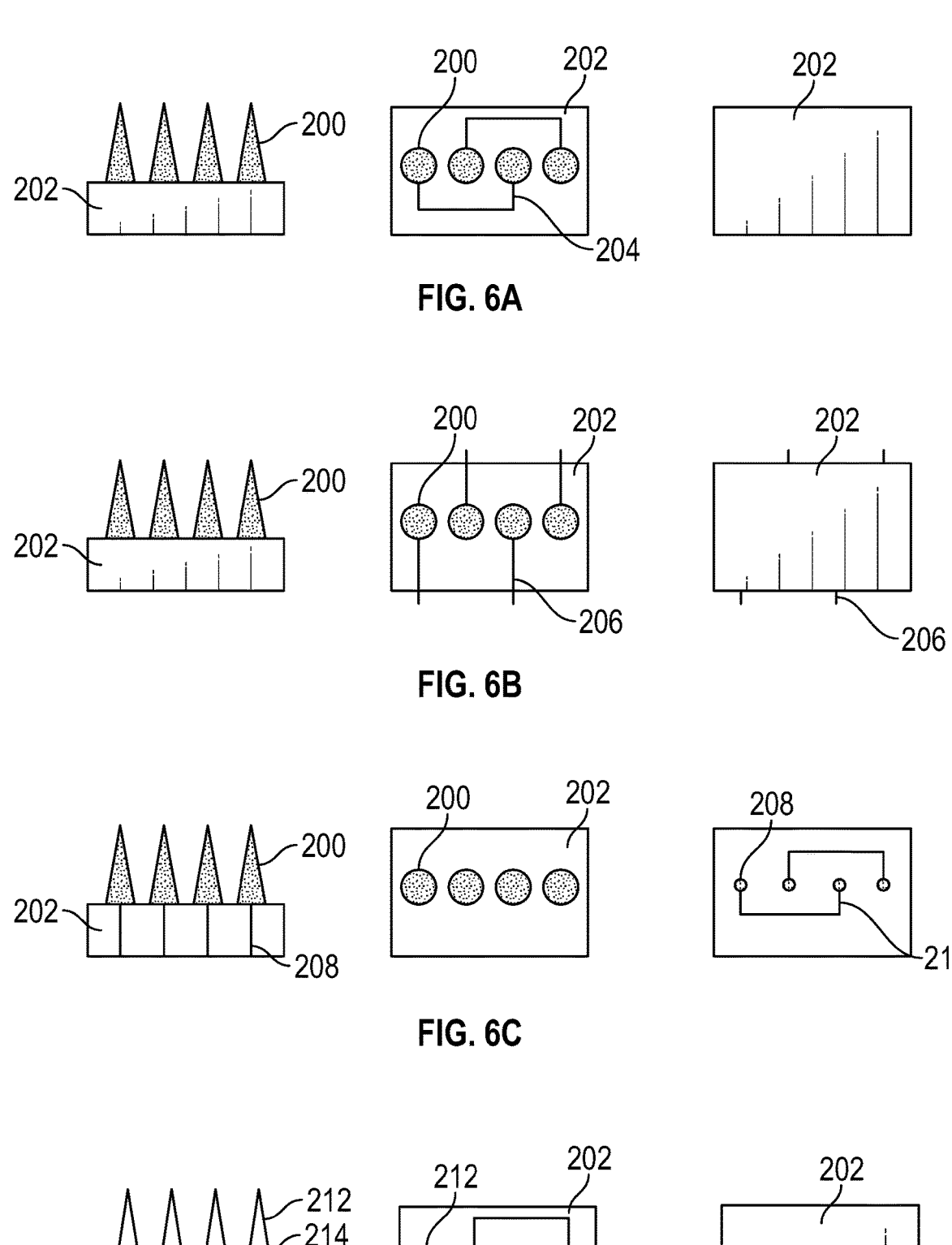
FIGS. 6A-6D are schematics of the electrical connections of microneedle electrode arrays, according to some embodiments of the present disclosure.

FIGS. 6A-6D show four embodiments of electrical connections of microneedle arrays. As shown in FIG. 6A, electrically conductive microneedle electrodes 200 are connected to an electrically non-conductive substrate 202. Electrical connections 204 (e.g., wires) on the upper surface of the substrate 202 (i.e., the same side of the substrate 202 to which the microneedle electrodes 200 are connected) selectively provide electrical connection between microneedle electrodes 200 of the same polarity.

As shown in FIG. 6B, electrically conductive microneedle electrodes 200 are connected to an electrically non-conductive substrate 202. Electrical connections 206 on the lower surface of the substrate 202 (i.e., the opposite side of the substrate 202 to which the microneedle electrodes 200 are connected) selectively provide electrical connection between microneedle electrodes 200 of the same polarity.

As shown in FIG. 6C, electrically conductive microneedle electrodes 200 are connected to an electrically non-conductive substrate 202. Electrical connections 208 go from the upper surface of the substrate 202 (i.e., the same side of the substrate 202 to which the microneedle electrodes 200 are connected) to the lower surface of the substrate 202. Electrical connections 210 selectively provide electrical connection between microneedle electrodes 200 of the same polarity.

As shown in FIG. 6D, electrically non-conductive microneedles 214 are connected to an electrically non-conductive substrate 202. Electrically conductive material 212 at least partially covers the surface of the microneedles 214 to form microneedle electrodes. Electrical connections 216 on the upper surface of the substrate 202 (i.e., the same side of the substrate 202 to which the microneedles 214 are connected) selectively provide electrical connection between electrically conductive material 212 forming electrodes of the same polarity.

Applications of the Devices and Methods

The methods described herein are used to administer agents, typically a drug, to patients with the aid of electroporation. As used herein, the term "electroporation" includes related phenomena known in the art, such as electrofusion, and may include viruses, virus-like particles, liposomes and any other particulate objects containing a lipid bilayer membrane. The patient may be a human or other mammal in need.

The methods advantageously may be used to deliver large molecule drugs into body tissues of the patient using electroporation without the use of batteries, capacitors, or other conventional electric power storage devices, and without the use of electricity from an external source (e.g. not plugged into an electrical outlet). However, a wide variety of drugs, including small molecules, proteins, nucleic acids-based compounds, and biologicas may have their delivery facilitated. The range of drugs includes biologics, which may be comprise of antigens (substances derived from or mimicking foreign substances to induce an immune response when introduced) synthetically synthesized in the form of nucleic acids or proteins or naturally obtained from relevant sources; nucleic acids such as DNA, RNA, or other polynucleotide compounds in plasmid or linear form; peptides (amino acid sequences); viral vectors or viruses; vaccines of any type; gene therapies such as CAR-T cell therapy to treat cancers; immunotherapies; chemically or biologically synthesized proteins; and/or any combination of these, or the drug loaded particles, such as lipid nanoparticles, polymeric nanoparticles.

In some embodiments, the electric field is localized to the skin and especially to the epidermis, where localization to the epidermis means that the majority of cells experiencing electroporation conditions are located in the epidermis and not in the dermis or deeper tissues. This localization is facilitated by the combination of limiting penetration of the electric field to deeper tissues and by the fact that cell density in viable epidermis is much greater than in dermis. Targeting the electric field and resulting electroporation to the skin and especially the epidermis improves immunogenicity and allows for reduced side effects. Unlike dermis, which is largely acellular, the epidermis is densely populated with cells, including keratinocytes as well as potent antigen-presenting cells, such as dendritic cells, including Langerhans cells. Targeting antigen to these epidermal cells has been shown to improve immune responses compared to IM injection. While electroporation of dermis has less value, diffusion of antigens produced in epidermal cells into the upper dermis is beneficial, due to the presence of dermal dendritic cells and a rich vasculature that enables drainage to lymph nodes, which also increases immunogenicity. Moreover, localizing the electric field to epidermis can reduce nerve stimulation, thereby making electroporation more tolerable. Of particular concern is stimulation of motor nerves and muscle cells below the skin, which can cause violent twitching reported for skin or muscle electroporation in other contexts. Indeed, this was shown in the examples disclosed herein, where conventional electroporation with the clamp electrode caused strong muscle contractions at the site of electroporation upon application of each pulse. The animals were anesthetized, which indicates a direct stimulation of action potentials in muscle cells and/or motor nerves. These contractions were not seen when electroporating with MEAs that localized the electric field superficially, far away from muscles.

The method of electric field localization differs from other methods in a few ways. Other approaches using penetrating electrodes that are much longer than the present microneedle electrodes. Those other penetrating electrodes completely cross the epidermis and dermis, and penetrate into the sub-dermal tissue and often deeper still. Because the present microneedle electrodes penetration into epidermis and possibly a portion of the dermis, the microneedle electrodes do not fully cross the dermis and do not contact tissues below the dermis. Because the electric field produced when pulsing these microneedle electrodes is strongest in the tissue between oppositely charged electrodes, tissue deeper than the penetration depth of the microneedle electrodes receives weaker electric fields that are less likely to cause electroporation.

Another approach to electroporating tissue involves the use of surface electrodes that contact the skin surface but do not penetrate into the skin. They may involve treatments of the skin surface to facilitate contact, such as application of conductive gel or other material or at least partial removal of the stratum corneum using sandpaper or other methods. In this case, the electric field penetrates into the skin to a depth that is similar to the spacing between the electrodes. This spacing in typical systems is at least millimeters or larger. As a result, the electric field is not concentrated in the dermis, and certainly not in the epidermis, but it reaches tissue below the dermis. It is possible to have very closely spaced surface electrodes (e.g., less than 1 mm) that better limit exposure of sub-dermal tissues to electric fields. However, they generate more heterogeneous electric field strength in the skin compared to penetrating microneedle electrode arrays.

The present invention may be further understood with reference to the following non-limiting examples.

EXAMPLES

Experiments were conducted to compare the devices and methods described herein to commercially available devices and methods.

Figure 7C:
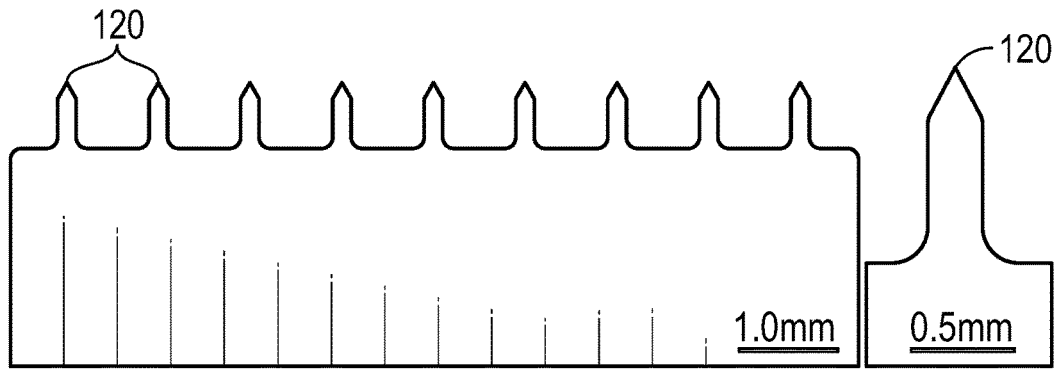
Figure 7D:
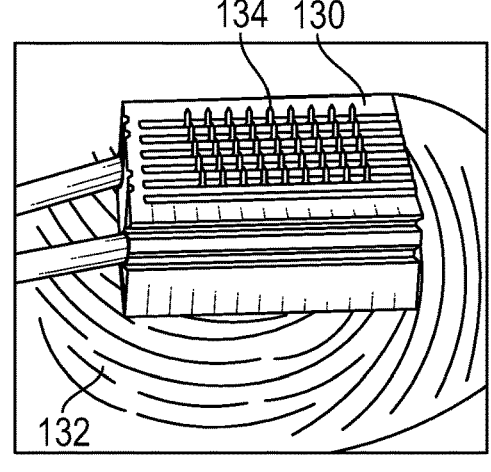
Figure 7E:
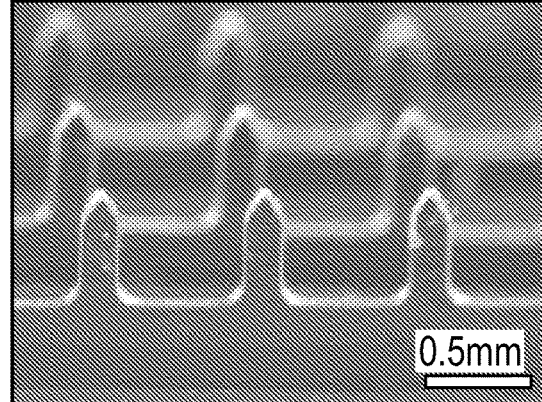
Figure 7F:
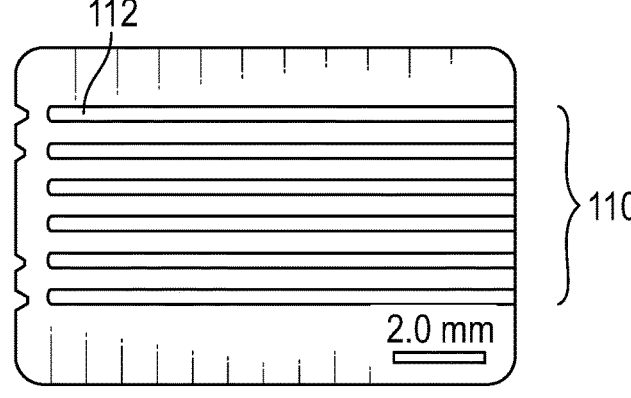

The microneedle electrode array (MEA) described in the following examples was fabricated by assembling 6 rows of stainless steel microneedles (electrodes) measuring 650 μm in length and 200 μm by 50 μm in cross-section that tapers to a sharp tip mounted in a 3D-printed insulating holder made of polylactic acid. Each row of electrodes with the same electrical polarity consists of 9 microneedles each separated by 0.8 mm spacing within each row (i.e., microneedle electrodes of the same polarity), and with rows separated by 0.9 mm spacing (i.e., separation of microneedle electrodes with opposite polarity). FIG. 7E (right) is a magnified view of electrode rows, according to one embodiment. This close spacing serves to enable the large electric field strength needed for electroporation using microsecond pulses. The piezoelectric pulse generator was connected to the MEA using wire for positive and negative terminals (See, e.g., FIG. 7D). In use, the MEA was pressed against the skin so that the microneedles penetrated across the skin's stratum corneum barrier to enter the viable epidermis and superficial dermis, after which the thumb toggle was pressed to administer the pulses (FIG. 7A). FIG. 7A show an electroporator 80 being held in a position by a hand 82 before activation. The electroporator 80 comprises a housing 86 having a toggle switch 84, which may be activated, for example, by a user's thumb. The electroporator 80 further comprises an MEA cartridge 88. FIG. 7B is an exploded view of the electroporator 90 comprising a piezoelectric pulse generator and a metal MEA, known as an ePatch. The piezoelectric pulse generator comprises a crystal case 96 housing the piezoelectric crystal 94. An MEA cartridge 102 comprising microneedles 100 is connected to the piezoelectric pulse generator via copper wires 98. The electroporator 90 further comprises a hand toggle 92. FIG. 7C shows a row of microneedle electrodes (left) and a single electrode 120 (right), FIG. 7D is a diagram showing a configuration of electrodes in one embodiment of an MEA, and FIG. 7E is a magnified view of a section of an MEA relative to a finger 132. In FIG. 7E, an MEA cartridge 130 holds the microneedles 134. FIG. 7F is a plan view of the polymeric holder/casing 110 for the plates of the microneedle electrodes which may connect to the holder 110 via slots 112.

The examples herein demonstrate that the methods and systems comprising a piezoelectric pulse generator and a metal MEA can selectively delivery molecules into cells in the epidermis using microsecond pulses with no evidence of significant damage to the skin. In contrast, electroporation using millisecond pulses from a conventional electroporation device can exhibit significant damage at the site of each microneedle electrode penetration in the skin. The methods and systems of the present invention can deliver a DNA vaccine and produce robust humoral immune responses and viral neutralization, demonstrating at least 10-fold dose-sparing compared to intradermal (ID) or intramuscular (IM) injection without electroporation.

Example 1—Electroporation Study in Animals Using Piezoelectric Pulse Generator and Microneedle Electrode Array Animal and Plasmid All animal experiments were performed in compliance with the Institutional Animal Care and Use Committee (IACUC) guidelines of Emory University and the Georgia Institute of Technology. Adult female Wistar rats (250-300 g) and 5-6-week-old female BALB/c mice were used. The animals were kept in a 12 h/12 h light/dark cycle at the animal care facility, given free access to diet and water, and acclimatized for at least 7 days before the experiments. The high expression reporter plasmid gWiz-GFP was used. The DNA of SARS-CoV-2 surface glycoprotein without transmembrane domain were cloned into pCAGGS vector with in-fusion cloning technology.

Design of Piezoelectric Pulse Generator and Microneedle Electrode Array

The device comprised a piezoelectric pulse generator and an electrically coupled MEA is referred to herein as "ePatch". The electric pulses were generated by a device derived from a common household piezoelectric stove lighter (FIG. 7B). A cylindrical chamber was 3D-printed for housing a piezoelectric crystal harvested from a commercial lighter. The chamber had a wire connected to the piezoelectric crystal and exited the chamber through its base. A hand toggle was attached at the top to provide the equivalent force utilized in a conventional lighter when it is pressed downwards. The holder was 3D printed with poly(lactic acid) by a 3D printer.

Figure 11B:
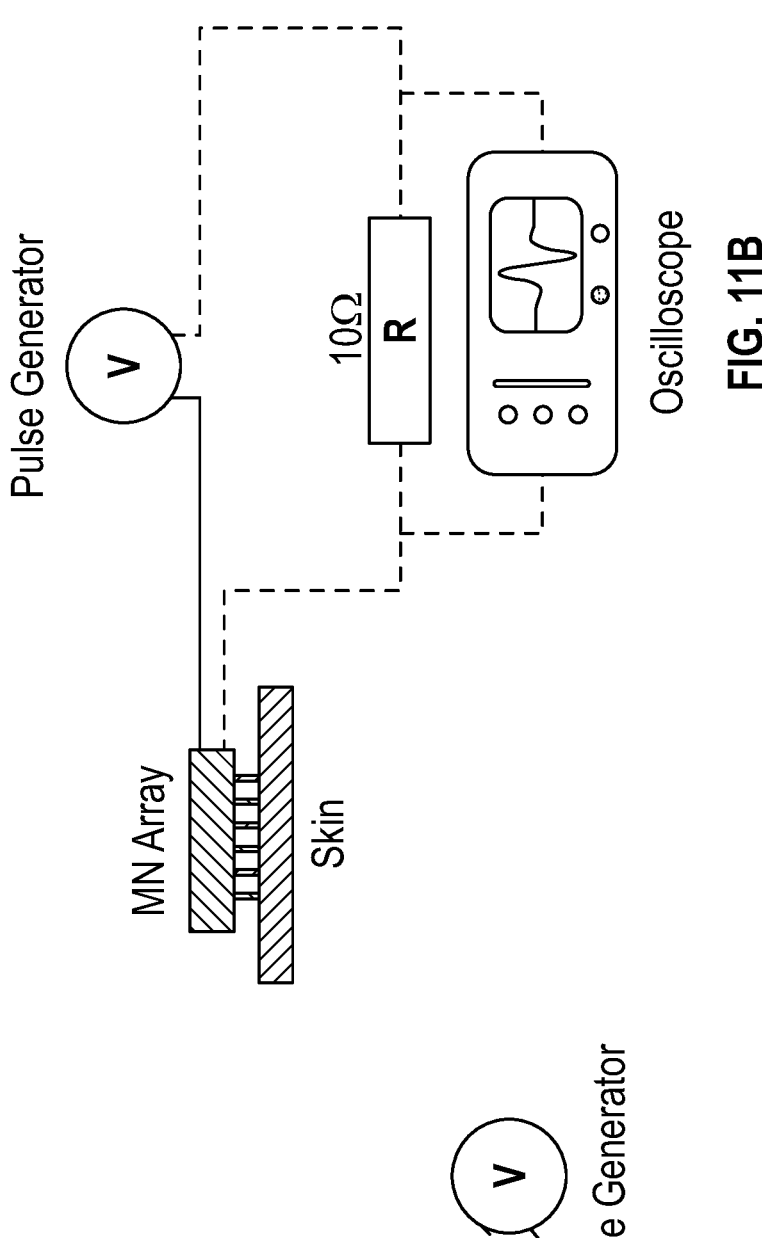
FIGS. 11A-11D depict the measurement of voltage and current during administration of electric pulses, according to embodiments of the present disclosure. Schematic illustrations of the electric circuits used for measuring the voltage (FIG. 11A) and current (FIG. 11B) during electroporation are shown.
Figure 11A:
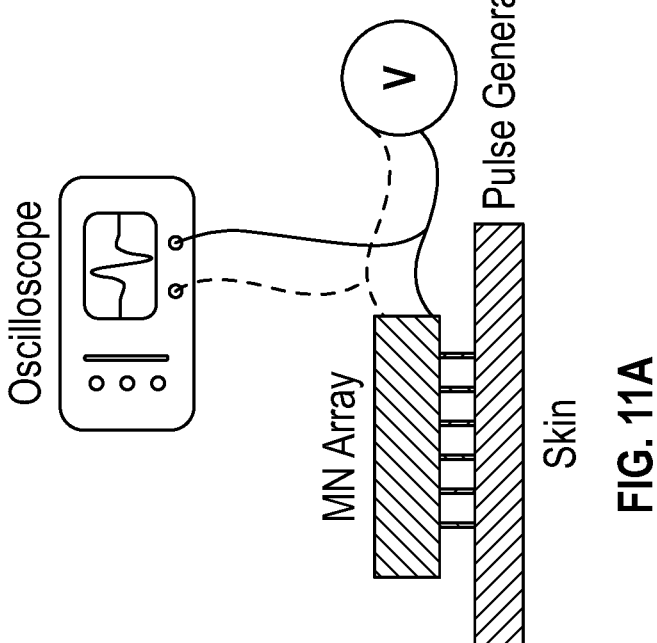

The MEA was fabricated by assembling 6 rows of solid metal microneedles in an insulative holder. Each row had 9 microneedles, each spaced 0.79 mm apart measured tip-to-tip. Microneedles with opposite electrical polarity were positioned adjacent to each other at a distance of 0.90 mm between rows. The pulse profiles from the ePatch device were measured by an oscilloscope (according to the electric circuit shown in FIGS. 11A-11B.

Numerical Simulation of Electric Fields for Electroporation

The electric field strength distribution was analyzed by numerical modeling using commercially available modeling software. The parameters for the numerical simulation of the electric field in the skin are shown below in Table 1.

TABLE 1

| Skin anatomy | Rat | Mouse | Resistance (S/m) |
|---|---|---|---|
| Stratum Corneum | 20 μm | 10 μm | 0.0005 |
| Epidermis and dermis | 650 μm | 150 μm | 0.2 |
| Subcutaneous layer | 1300 μm | 300 μm | 0.05 |

To simplify the model, the conductivity changes of the permeabilized tissues during electroporation was not considered, thereby capturing the peak electric field strengths at the beginning of a pulse applied to previously untreated skin. The electric field simulation was done in electrostatic mode, where the rows of metal needle electrodes were set to static high and low potentials alternatively such that the voltage between the adjacent rows met the target voltage value. The medium between the needle tip sections was set using skin parameters to mimic the scenario when the microneedles penetrate skin. Results from using this model are presented in Examples 5 and 7.

Discrimination of Non-Viable Cells and Electroporated Cells Via Confocal Microscopy To study the effect of electroporation on cell viability and cell permeability in the skin, a cell-impermeable probe, SYTOX Green, was used to identify uptake by the transient cell membrane permeability caused by electroporation. SYTOX Green was coated on the microneedles before electroporation and used as an indicator for the transient permeability caused by electroporation. Another cell-impermeable probe, ethidium bromide (EB), was used as an indicator of non-viable cells caused by electroporation. BALB/c mouse skin was used as the tissue model.

Under anesthesia, the dorsal dermal hair was removed with a shaver, then depilatory cream was applied for 3 min. The skin was cleaned with wet gauze to remove the depilatory. Three days after hair removal, the mice were anesthetized with isoflurane, a MEA was pressed into the skin, and 5 or 20 piezoelectric pulses were applied. The mice were euthanized with carbon dioxide 10 min after electroporating the skin. The skin was harvested and submerged in phosphate-buffered saline (PBS) containing EB (50 μg/ml), incubated at 4° C. and shaken for 1.5 h. The skin was washed 3 times with fresh PBS and imaged using a Laser Scanning Confocal Microscope (20× objective) (not shown). SYTOX Green and EB were sequentially excited using an argon laser at 488 nm and 514 nm, respectively. Under the confocal microscope, the non-viable cells had red fluorescence from EB and the electroporated cells had green fluorescence from SYTOX Green (not shown).

Live Imaging of GFP Expression and Histological Examination of the Skin

Rats were prepared under anesthesia one day before DNA delivery studies by removing hair on their dorsal skin using a clipper, after which depilatory cream was applied for 4 min and wiped clean with water. The animals were anesthetized in an induction chamber charged with 5% isoflurane in $O_2$ by isoflurane vaporizer and then fitted with a standard rodent mask and kept under general anesthesia during the procedures.

Twenty microliters of PBS containing GFP plasmid (2.5 µg/µl) was injected ID to form a visible bleb in the skin. Electroporation pulses were applied to the injection site either with MEA or clamp electrodes 1 min after injection of the DNA. A specified number of microsecond pulses (1, 5, 10, 20 pulses) were generated by the ePatch device to investigate the effect of pulse numbers on gene expression. A commercial benchtop electroporator with programmable pulse voltages was also used to study the effect of voltages of millisecond pulses on gene expression. The fluorescence intensity of GFP in the skin was monitored by an IVIS Spectrum CT In Vivo Imaging System on different days.

For histological examination studies, mouse skin in vivo was electroporated with 20 pulses by the ePatch device, and imaged under stereo microscope immediately after electroporation and again 3 h later. After the skin was harvested 12 h after electroporation, the tissue was embedded in Tissue-Plus O.C.T. Compound and frozen at −20° C. overnight before sectioning at 20 µm thickness using a freezing microtome. Tissue sections were imaged by laser scanning confocal microscopy (not shown). For H&E staining, the tissue was fixed overnight in 10% formalin buffer, then dehydrated by an automatic tissue dehydration system. The dehydrated tissue was embedded in paraffin, sectioned at 5 µm thickness by rotary microtome, and stained. The tissue was imaged by inverted microscope (not shown).

Immunization Study in Mice

For the mouse immunization study, it was confirmed that the same electroporation parameters used in rats similarly produced strong GFP expression in mouse skin. BALB/c mice were randomized into five groups (n=5 mice per group) that received injection of 10 µl solution containing SARS-CoV-2 S protein DNA vaccine in PBS: (i) 10 µg DNA vaccine by IM injection, (ii) 100 µg DNA vaccine by IM injection, (iii) 10 µg DNA vaccine by ID injection, (iv) 10 µg DNA vaccine by ID injection followed by 20 pulses by the ePatch device, and (v) PBS by ID injection as a negative control. The mice were anesthetized during the procedures by isoflurane. Each animal received a second dose after 4 weeks via the same procedures as the first dose. At week 7, blood was withdrawn by orbital sinus puncture, and the serum was separated.

ELISA for SARS-CoV-2 Spike Protein Antibody Analysis

Enzyme-linked immunosorbent assay (ELISA) was used to measure the titer of IgG against the spike surface protein of SARS-CoV-2 in the mouse serum. ELISA plates were coated with purified spike protein, then blocked with 5% bovine serum albumin. Serum samples were diluted 80-fold with PBS containing 0.1% Tween 20 (PBST), then added to the ELISA plates and incubated at room temperature (20-25° C.) for 1 h, followed by washing three times with PBST. Horseradish peroxidase-conjugated goat anti-mouse antibodies were added and incubated for 1 h. The plates were washed again followed by the addition of 3,3',5,5'-tetramethylbenzidine substrate to develop color. The reaction was terminated by commercial stop solution. The absorption was read at 450 nm by an ELISA plate reader. Optical density (OD) values were recorded and used as relative antibody expression levels in mice.

Pseudovirus Neutralization Assay

The SARS-COV-2 spike protein pseudotyped virus was used in the neutralization assay. The pseudoviruses were produced by co-transfection of 293T cells with an env-deficient HIV-1 backbone plasmid DNA and a DNA plasmid expressing the full-length SARS-CoV-2 spike protein flowing established protocols. The pseudoviruses were produced and self-packaged in 293T cells. The pseudovirus that was secreted into the supernatant of 293T cells was collected.

For analysis of serum neutralizing activities, 293T cells expressing angiotensin-converting enzyme 2 (ACE2) were seeded in a 96-well plate and grown overnight. Mouse serum samples were diluted 100-, 300-, and 900-fold with Dulbecco's Modified Eagle Medium. Each diluted sample (50 µl) was mixed with an equal volume of virus suspension (50 µl), followed by incubation at 37° C. for 1 h. Then, the samples containing the serum-pseudovirus mixture were added in triplicate to the wells of the 96-well plate seeded with ACE2-expressing 293T cells that were grown to 50% confluency. Six hours after infection, the suspensions were centrifuged at 1500×g for 5 min, and the supernatant was removed and replaced with DMEM containing 5% fetal-calf serum. After 48 hours, the cells in each well were lysed and the luciferase activity was determined. The neutralizing activity of immune sera was determined by the formula: [(pseudovirus alone)−(pseudovirus+sera)]/[pseudovirus alone]×100%.

Example 2—Preliminary Pig Skin Test

First, a preliminary fluorescence study using pig skin was used to compare a traditional microneedle injection platform to a delivery system which consists of a piezoelectric pulse generator operably coupled to an array of microneedle electrodes. In particular, SYTOX Green was used to monitor expression. A red dye, Ethidium Bromide, was also used to indicate cells killed due to injection. The pig skin was injected using a traditional microneedle platform and the cells were imaged (not shown). The pig skin was also injected using a new delivery system of the piezoelectric pulse generator with an array of microneedle electrodes. Images were taken at 0 pulses, 5 pulses and 10 pulses (not shown). Not only was expression significantly higher using the new delivery system compared with the conventional microneedle platform, there was no significant loss of cell viability due to the injection.

Example 3—Gene Transfection in the Epidermis

To assess targeting of gene transfection to the epidermis, a histological analysis 1 day after DNA delivery was performed. Electroporation with MEA using either microsecond pulses from an "ePatch" device, consisting of a piezoelectric pulse generator and a metal MEA, and using millisecond pulses from the commercial benchtop electroporator (BTX Electro Cell Manipulator 600, Harvard Apparatus, Cambridge, MA resulted in strong green fluorescence evident across the skin surface exposed to the MEA when viewed en face on the skin surface, and throughout the viable epidermis, with little evidence of GFP expression in dermis or stratum corneum, when viewed as a frozen histological section. The images showed that the transfected cells were almost exclusively identified within the epidermal layer beneath the stratum corneum (not shown). In contrast, when electroporation was carried out using the clamp electrode, GFP fluorescence was less intense (consistent with the quantitative findings in shown in FIG. 9). Moreover, although the transfected cells were mostly in the epidermis, evidence of GFP transfection in the deep dermal layer, notably in the hair follicles was seen. These findings confirm the ability of the MEA to localize electroporation to the epidermis.

Example 4—Analysis of High-Voltage Pulses and
Electric Field

Figure 8A:
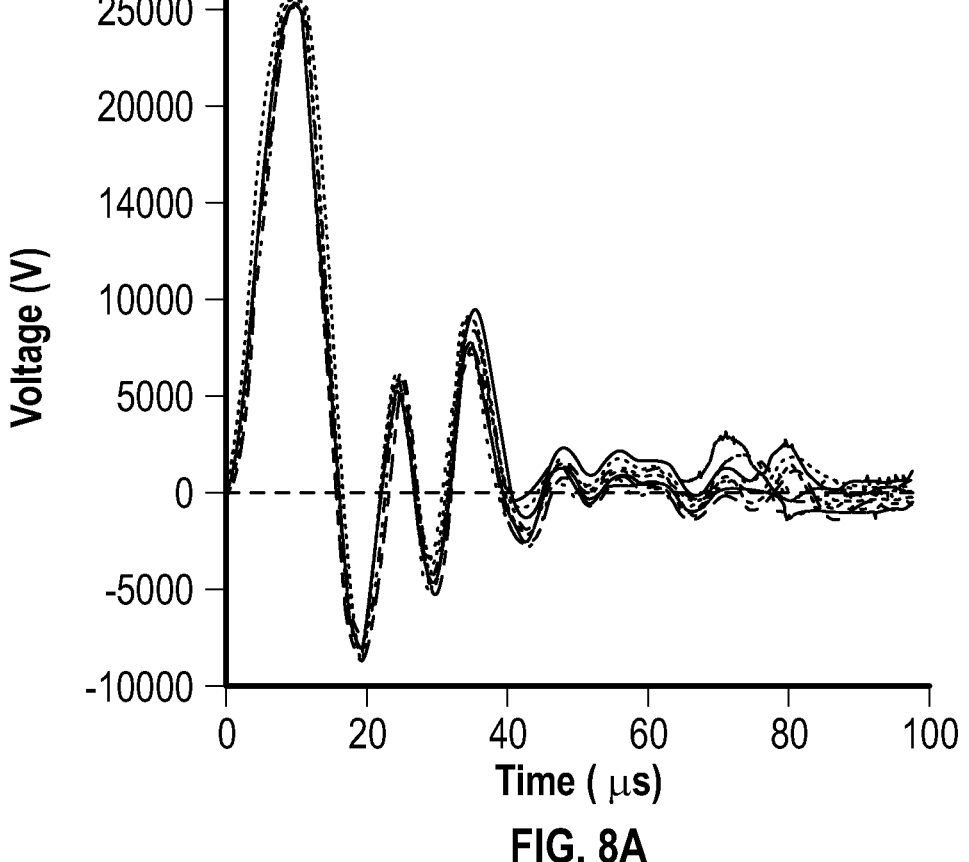
FIGS. 8A-8C are graphs of representative electrical output profiles for a piezo-electric pulser used for electroporation, according to one embodiment of the present disclosure.
Figure 8B:
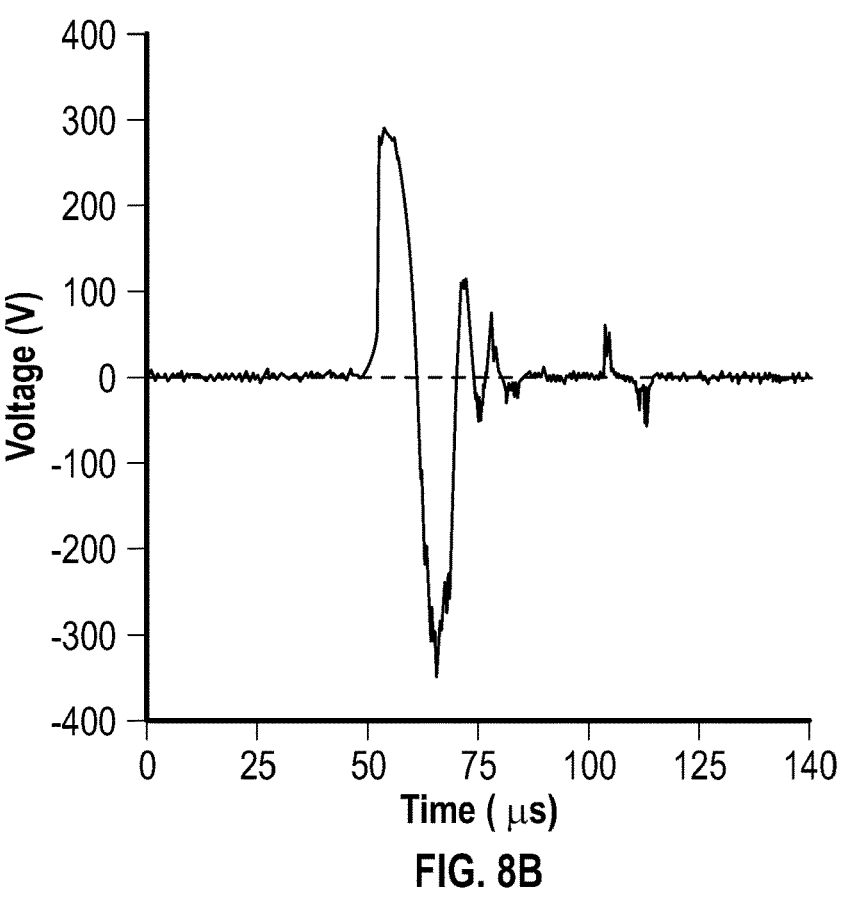
Figure 8C:
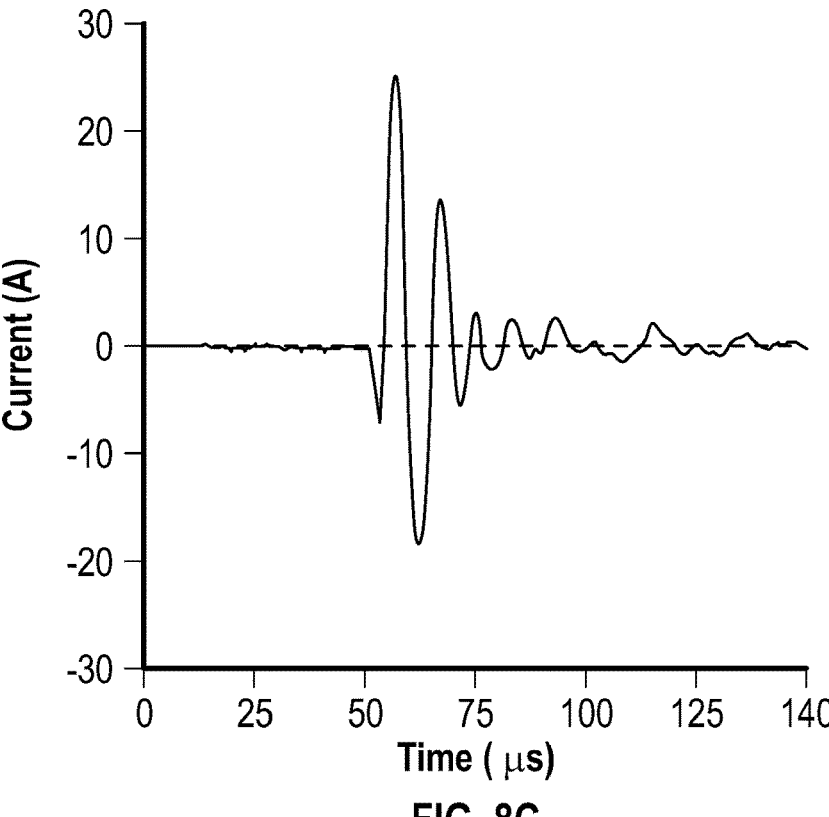

Using a high-voltage probe and oscilloscope, the voltage outputs from an ePatch through air sparking without skin penetration were determined. FIGS. 8A-8C show representative electrical output profiles for a piezo-electric pulser used for electroporation. A piezo-electric pulser was activated by attaching the electrode leads directly to the oscilloscope probe (a, voltage profile) and by pulsing in porcine skin ex vivo (FIG. 8B, voltage profile; FIG. 8C, current profile). In FIG. 8A, multiple replicate voltage profiles are shown (n=20). The outputs generated pulses with peak positive static voltages and peak negative static voltages of 24.4±1.3 kV and −7.0±0.8 kV, respectively (FIG. 8A). Given the electrode spacing of 0.9 mm, this corresponds to a peak positive static field strength of 1200 kV/cm, which is higher than the dielectric strength of air (i.e., —30 kV/cm). The peak positive static voltage was achieved after 10.6±0.7 µs and the oscillating voltage output that followed decayed within ~100 µs (FIG. 8A). This extremely high static voltage was enabled by the very high electrical impedance and lack of current.

Figure 11C:
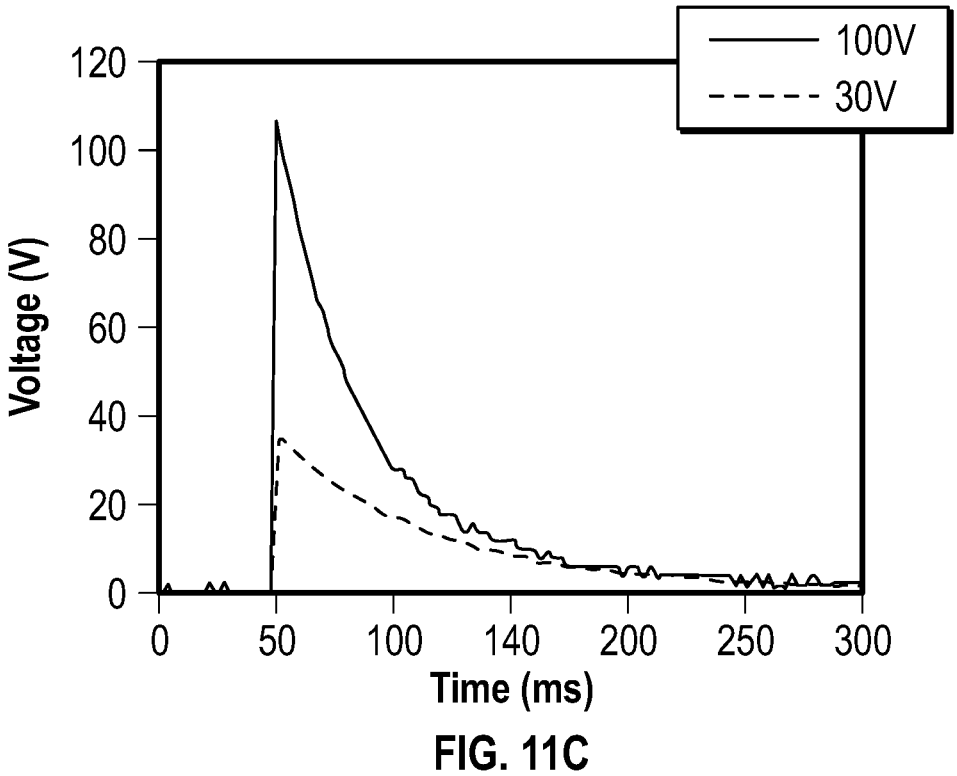

While applied to porcine skin ex vivo using an MEA as electrodes, the peak positive and negative voltage outputs were 283±49 V and −345±54 V, respectively (FIG. 8B). Voltage measurements were made using the setup shown in FIG. 11A. The time to peak voltage was 12.6±1.1 µs. Here, the voltage was much lower due to the lower impedance of skin compared to connection to the oscilloscope, which allowed passage of current throughout the pulse duration. The electric pulses were in the form of a bipolar oscillating decaying waveform, which is characteristic of piezoelectric pulses. For a comparative analysis, electric pulses using a commercial bench electroporator commonly employed for laboratory transfections were also generated and coupled to a MEA in porcine skin ex vivo. This pulser generated monopolar exponential-decay pulses of 31±3 V or 100±5 V with 59.2±7.8 ms or 55.4±2.3 ms pulse durations (i.e., exponential decay time constant), respectively (FIG. 11C). These millisecond, monopolar pulses are more typical of those used for conventional electroporation, which contrasts with the microsecond, oscillatory pulses generated by the ePatch.

Figure 11D:
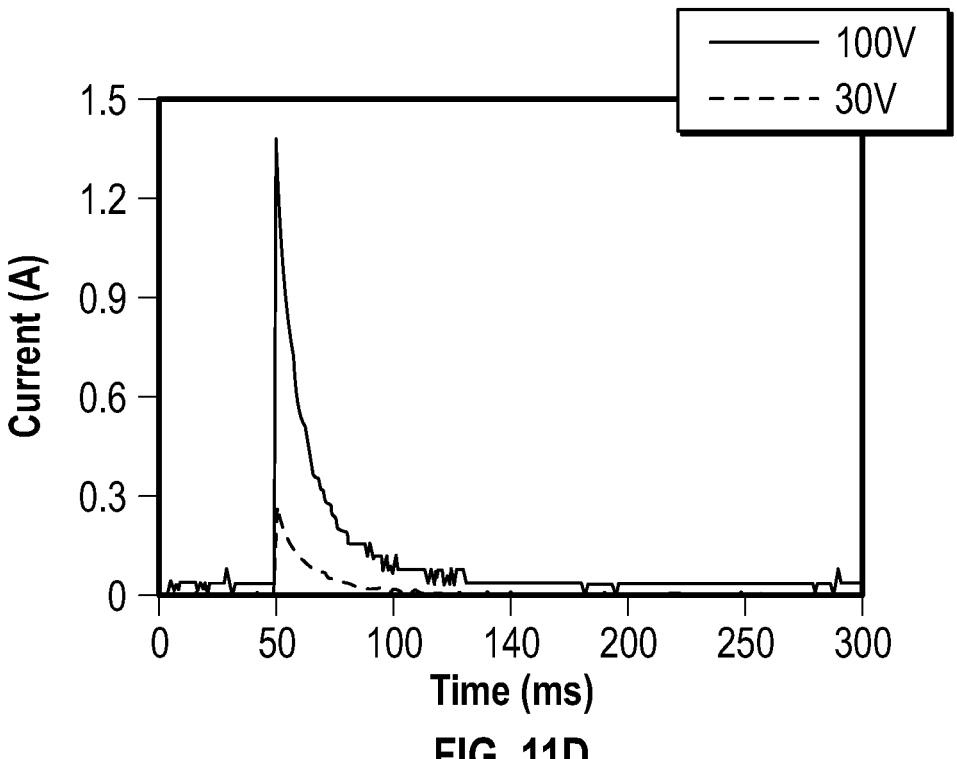

The electric current through the skin during pulses from the ePatch device was also measured, which showed an oscillating decaying waveform that was similar in shape to the voltage waveform, and achieved a peak positive current of 24.8±1.1 A (FIG. 8C). Current measurements were made using the setup shown in FIG. 11B. For the commercial benchtop electroporator, the highest currents through the skin were 0.28±0.03 A and 1.33±0.16 A when 32±3 V and 105±4 V pulses were applied, respectively (FIG. 11D). The apparent electrical impedance (i.e., characterized as peak voltage divided by peak current) was 11.4Ω during ePatch pulsing and 114Ω or 78.9Ω during pulsing by the conventional electroporator (at 32 V or 105 V, respectively). The much lower apparent electrical impedance measured using the microsecond pulses from the ePatch versus the millisecond pulses from the conventional pulser may be explained by the reduced impedance known to occur in skin and other tissues exposed to electric fields with complex waveforms having higher frequency components.

Figure 12:
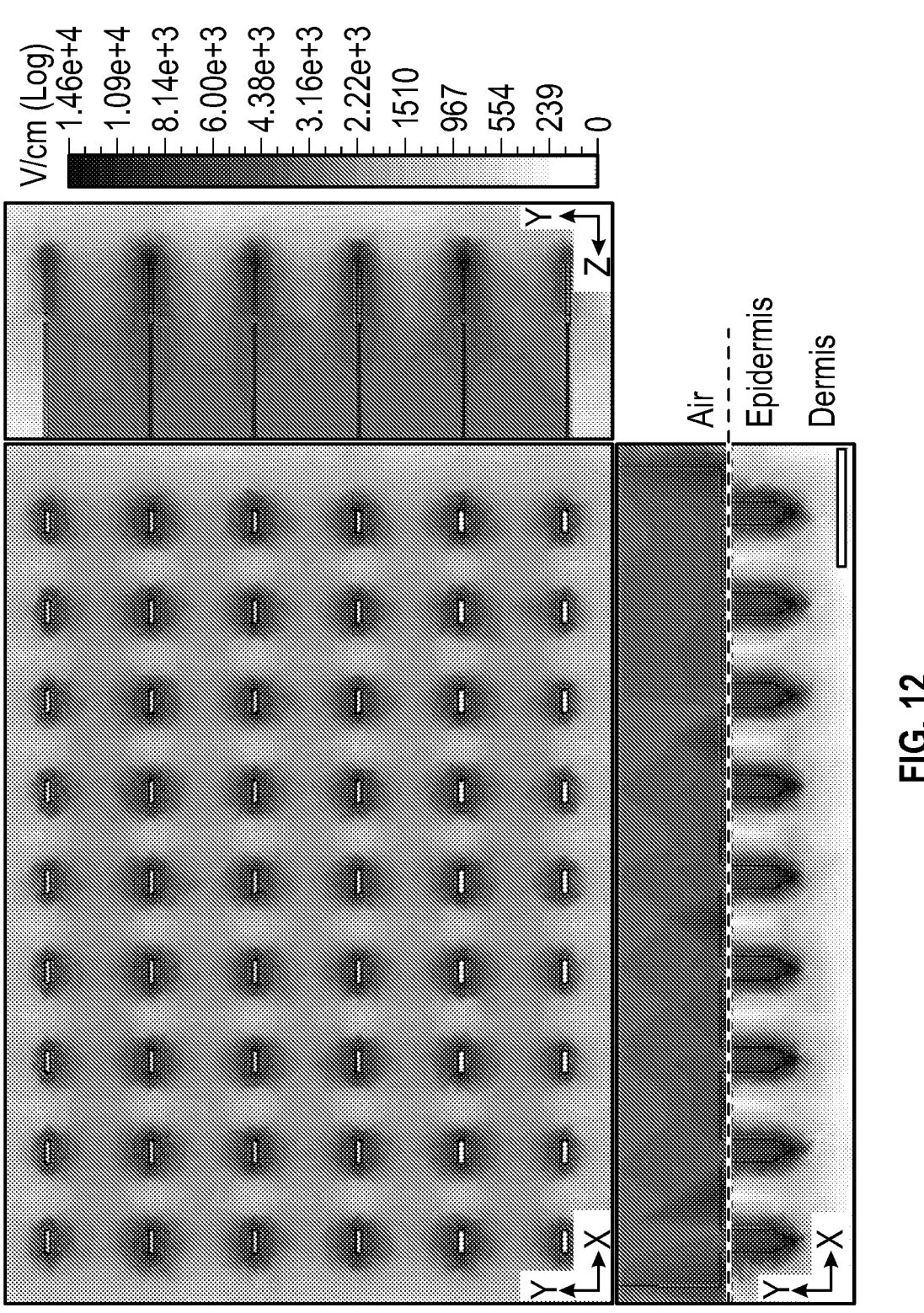
FIG. 12 is a computer simulation result showing the electric field strength distribution in skin produced by one embodiment of an electroporation device as described herein.

To better understand the electric field distribution in the skin when applying pulses using a MEA, the electric field strength in the skin during electroporation was modeled, as shown in FIG. 12. FIG. 12 shows the electric field strength distribution in the skin determined by computer simulation. Peak electric field strength is shown when applying a 300 V pulse like those from the ePatch using a (a) MEA or (b) clamp electrode. Field strength distribution is shown from above the MEA (upper left) and as side views (bottom and right). The dermal-epidermal junction is indicated by the dashed line. The scale bar is 1 mm.

For the MEA, the electric field strength was highest surrounding each microneedle electrode, especially near the tip, where electrode curvature is known to increase electric field strength (FIG. 12). The electric field strength was weakest between electrodes of the same polarity. The electric field also did not penetrate deeply into the tissue below the electrodes, dropping off on a length scale of hundreds of microns. In this way, the electrical field was localized to the epidermis and upper layer of the dermis, which contain abundant antigen-presenting cells, such as epidermal Langerhans cells and dermal dendritic cells, and has efficient drainage to lymph nodes, all of which can enhance vaccine immunogenicity.

The threshold value for reversible electroporation depends on the duration of exposure to the electric field. For the millisecond-long pulses, the electroporation threshold in is expected to be on the order of 400-600 V/cm, while for the microsecond pulse duration, the threshold is increased to 1.0-1.5 kV/cm. When applying 300 V pulses using the piezo-electroporator, the highest electrical field strength in the tissue is 15 kV/cm immediately next to the electrodes, but most of the tissue experienced field strengths of 2-3 kV/cm, which is higher than the threshold necessary for successful electroporation, but still low enough to avoid extensive cell killing. In this way, highly localized cell death adjacent to the electrodes may be expected as well as small regions that are not electroporated between electrodes of the same polarity, but most tissue experiences a field strength expected to cause reversible electroporation.

These findings were further compared to the field strength in the skin generated using a conventional clamp electrode at the same voltage (300 V); it was found that the large spacing (i.e., 3.9 mm) of the clamp electrode produced much weaker electric field strengths compared to the MEA. The field strength only exceeded 1 kV/cm in a portion of the space between the electrodes, and only went above 1.5 kV/cm at the very edges of the electrode.

The field strength in the skin during application of representative pulses from a conventional electroporator (30 V and 100 V) using a clamp electrode or MEA was also investigated. The 30 V pulses with clamp electrode produced very low field strengths mostly below 300 V/cm, which does not achieve the expected electroporation threshold for millisecond pulses. Application of 30 V pulses with the closely spaced MEA enabled tissue immediately adjacent to the electrodes to reach 400-600 V/cm, but most of the tissue experienced much weaker electric fields. When using 100 V pulses, the clamp electrode achieved field strength expected to electroporate in some of the tissue, and the MEA produced electric fields strong enough for electroporation in most of the tissue.

Example 5—Robust Reporter Gene Transfection by
ePatch

To evaluate the effects of the ePatch device on plasmid delivery and transfection, Green Fluorescent Protein (GFP)-encoding DNA plasmid was delivered to rat skin in vivo. The level of gene expression was measured by in vivo imaging of GFP fluorescence over time.

Figure 9:
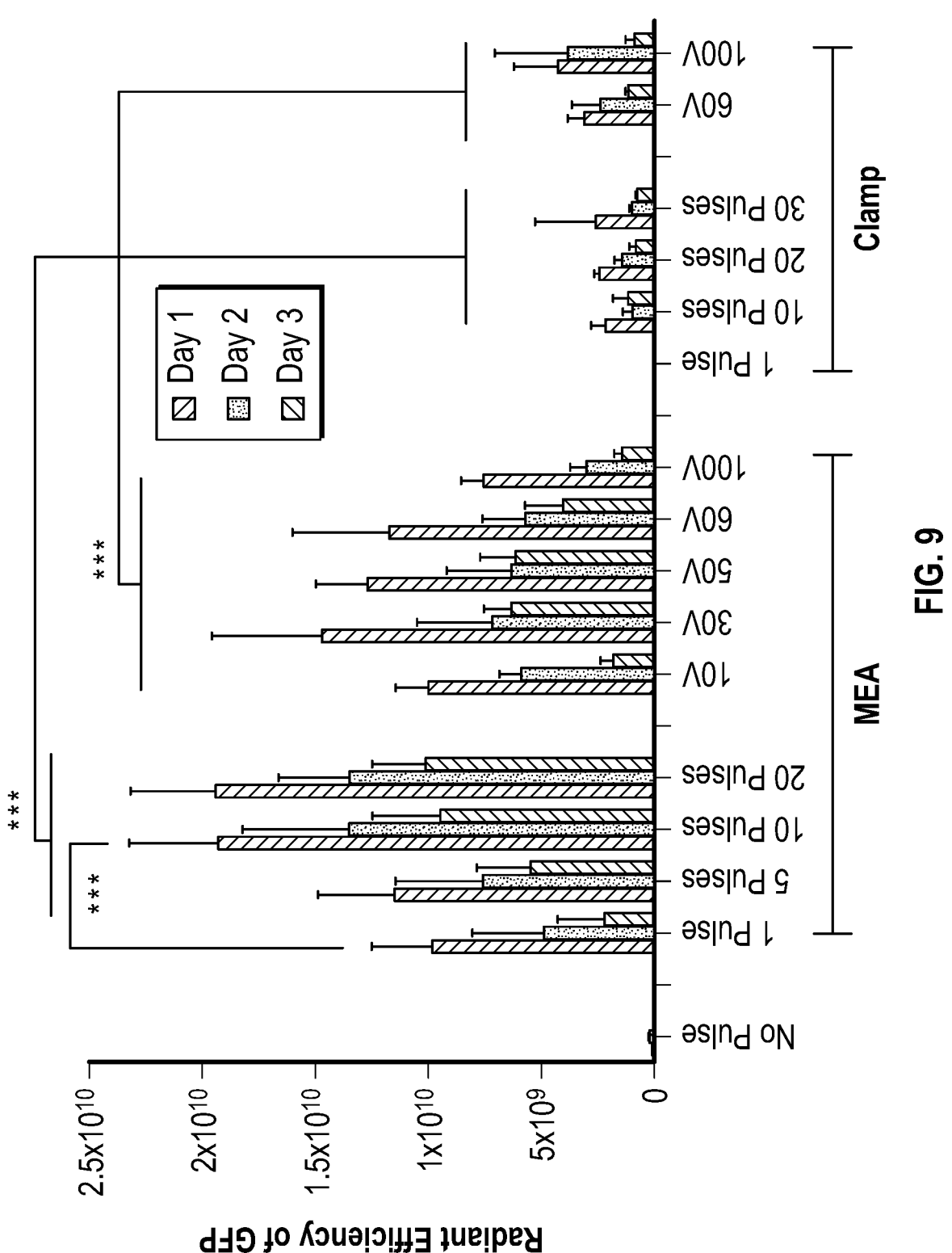
FIG. 9 is a graph showing GFP expression in rat skin after electroporation using a microneedle electrode array (MEA) or a clamp electrode.

The effect of high field strength, microsecond pulses using the ePatch, was tested and it was found that a single pulse was able to generate visible GFP expression (FIG. 9). FIG. 9 shows radiant efficiency of GFP fluorescence in the skin on different days after delivery of GFP reporter plasmid by electroporation using an ePatch giving 1-20 pulses of ~300 V with a waveform like that shown in FIG. 8B or using a conventional exponential-decay electroporation pulser at controlled peak voltage (10-100 V) with decay time constants (tau=49-57 ms). Pulses were applied using a microneedle electrode array (MEA) or a clamp electrode. Data represent mean±standard deviation (n=5-6 replicates per condition). (***p<0.001).

More pulses increased GFP expression up to 10 pulses (p=0.001); increasing to 20 pulses did not increase GFP expression further (p>0.05). For three days after electroporation, GFP expression decreased over time (p=0.002). After 5 days, GFP fluorescence was undetectable, likely due to GFP protein degradation in the skin.

As a negative control, an ID injection of the GFP plasmid into skin was performed without electroporation, which resulted in barely detectable GFP transfection (FIG. 9). The ePatch increased GFP expression 416-fold relative to ID injection alone (p<0.001).

To better interpret these results, additional experiment with a cell-impermeable green marker compound (SYTOX Green) present during electroporation to identify permeabilized cells was carried out and a red viability stain added afterwards to identify non-viable cells. Inspection of the skin by microscopy showed that there was loss of cell viability at the sites of microneedle puncture into skin, independent of electroporation, as indicated by the presence of red-fluorescent cells (not shown). This was probably due to damage from mechanical puncture by the microneedles. Application of 5 or 10 electroporation pulses from the ePatch did not appear to increase cell viability loss, but did cause increased cell permeabilization with uptake of the green marker compound into viable cells surrounding the nonviable core at the site of each microneedle penetration. Microscopic examination of the skin surface showed only faint and transient evidence of skin damage at the sites of each microneedle electrode penetration, as discussed below.

The effect of moderate field strength, millisecond pulses using the MEA coupled with the commercial electroporator was tested next. Electroporation under these conditions yielded GFP expression that peaked at 30 V (p=0.02) (FIG. 9). The peak GFP expression at 30 V was not significantly different to the peak value generated by the ePatch with 10 pulses (p=0.055), whereas GFP expression at other voltages was significantly lower (p<0.05). Similar to the ePatch, cells transfected by electroporation using millisecond pulses also had a decay in GFP fluorescence for 3 days after electroporation (p=0.008).

The dependence of GFP expression on voltage can be explained by a lesser degree of electroporation at 10 V versus 30 V, resulting in less transfection. Above 30 V, possible increased DNA delivery into cells was likely offset by increased loss of cell viability caused by irreversible electroporation and tissue heating during the millisecond-long exposure to high electric field strengths. This interpretation is supported by additional skin imaging after delivery of the green maker compound and application of the red viability stain (not shown). Increased loss of cell viability is seen with increasing voltage, and tissue heating at the sites of microneedle electrode placement increased as well, reaching peak values up to 50° C. Microscopic examination of the skin surface showed discoloration at the sites of each microneedle electrode penetration that persisted for at least two days, consistent with the observation of extensive cell death at the higher voltages using millisecond pulses (not shown).

To address current methods of skin electroporation, clamp electrodes (3.9 mm spacing) instead of MEAs were employed. When pulsing with the microsecond piezoelectric pulse generator, a single pulse did not result in detectable GFP expression, but applying 10, 20 or 30 pulses produced GFP expression that was independent of the number of pulses (p>0.05). Using the clamp electrode with millisecond pulses from the commercial electroporator, detectable GFP expression was found at 60 V, and was slightly increased when the voltage increased to 100 V (p>0.05). The GFP expression was significantly lower with the clamp electrode than when using the MEA with either ePatch or commercial electroporator (p<0.001).

Altogether these results demonstrate that (i) high levels of DNA transfection and expression can be achieved by the ePatch, (ii) using the MEA produced a high enough electric field strength to make the microsecond pulses from the piezoelectric pulser effective and (iii) enabled a conventional electroporator to be effective at much lower voltages compared to the clamp electrode, and (iv) the microsecond pulsing minimized tissue heating that appears to damage tissue when using millisecond pulses.

Figures 10A, 10B:
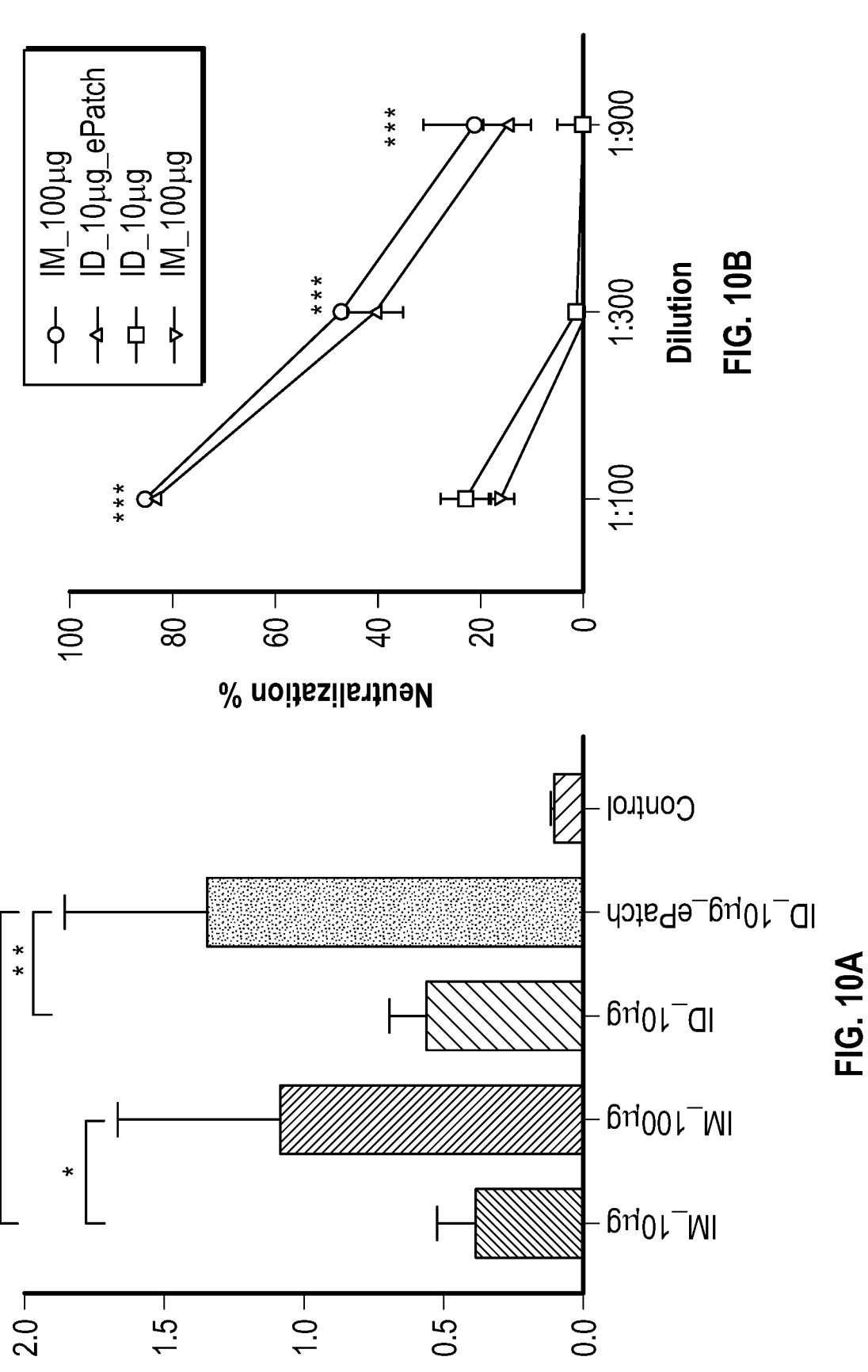
FIGS. 10A-10B are graphs showing the humoral immune response (FIG. 10A) and viral neutralization (FIG. 10B) after SARS-CoV-2 DNA vaccination in mice.

Example 6—Robust Immune Response and Viral Neutralization after SARS-CoV-2 DNA Vaccination in Mice After confirming that the ePatch can significantly augment gene expression in vivo, the immunogenicity of a SARS-CoV-2 DNA vaccine delivered by the ePatch, ID injection without electroporation, and IM injection without electroporation, including IM vaccination were evaluated at two different doses (10 μg and 100 μg DNA). IM vaccination produced humoral immune responses that were higher at the 100 μg dose than the 10 μg dose, as measured by antigen-specific IgG titers (p=0.04) and virus neutralization assay (p<0.001) (FIGS. 10A-10B). Specifically, the mice were immunized at week 0 and week 4; blood samples were withdrawn at week 7. IgG titer against SARS-CoV-2 spike surface protein in the mouse serum was expressed as absorbance at 450 nm (FIG. 10A). Neutralization of IgG against pseudovirus was analyzed at different dilutions of serum and expressed as neutralization percent for each dilution (FIG. 10B). For a control, mice were immunized by PBS. IM_10 μg and IM_100 μg: mice immunized with 10 μg and 100 μg DNA vaccine by IM injection, respectively. ID_10 μg: mice immunized with 10 μg DNA vaccine by ID injection. ID_10 μg_ePatch: mice immunized with 10 μg DNA vaccine by ID injection followed by electroporation using 20 pulses by ePatch. n=5 mice per group. (*p<0.05, p<0.01, *p<0.001).

ID injection of 10 μg DNA vaccine yielded results similar to IM vaccination at the same dose (p>0.05). When ID vaccination was carried out with electroporation by ePatch, immune responses were significantly higher than for ID or IM vaccination without electroporation at the same DNA dose (p=0.01 and 0.004, respectively). Moreover, ePatch vaccination with 10 μg DNA was not significantly different from IM vaccination with 100 μg DNA (p=0.47), demonstrating at least a 10-fold dose sparing enabled by ePatch vaccination. Finally, it is worth noting that with a 100-fold dilution of serum, 90% neutralization of antibody against SARS-CoV-2 pseudovirus was found for the low-dose ePatch and the high-dose IM injection groups, while only 20% neutralization was found for the low-dose IM and ID injection groups without electroporation (FIG. 10B). Altogether, this study demonstrates that the ePatch significantly improved immune responses to SARS-CoV-2 relative to IM or ID injection alone.

Clinical and histological examination suggests that vaccination using the ePatch was very well tolerated. Imaging of the skin surface immediately after electroporation showed evidence of microneedle puncture and/or localized electroporation when viewed with magnification (not shown). Subsequent imaging after 3 hours exhibited no residual evidence of the vaccination procedure. Histological examination of skin 12 hours after ePatch vaccination showed no inflammatory markers. In contrast, high voltage (100 V) millisecond pulsing caused extensive infiltration of inflammation cells seen in the skin 12 h after electroporation. Clinical exam of the animals over the weeks that followed vaccination produced no significant findings. These data suggest that ePatch vaccination caused only mild, transient effects to skin that do not raise safety signals.

Overall, the delivery systems and methods of the present disclosure were able to provide a DNA vaccination method that benefits from the combination of two innovations: a piezoelectric-based power source for electroporation and a MEA that generates large electric fields targeted to the epidermis. This combination, in the form of the ePatch, was shown to enable DNA vaccination using a simple, ultra-low-cost system that can expand the reach and speed of vaccination against COVID-19 and future pandemics.

The delivery systems and methods of the present disclosure were able to provide expression levels orders of magnitudes greater than a conventional injection without electroporation.

Modifications and variations of the methods and systems described herein will be obvious to those skilled in the art from the foregoing detailed description. Such modifications and variations are intended to come within the scope of the appended claims.

That which is claimed is:

1. A device for use in administering a drug into or across a biological tissue in a patient, comprising:
   a piezoelectric pulse generator; and
   an array of microneedle electrodes electrically coupled to the piezoelectric pulse generator,
   wherein the device, following insertion of the microneedle electrodes into the biological tissue, is configured to generate and deliver one or more electrical pulses through the microneedle electrodes effective to electroporate cells in the biological tissue and enable delivery of a drug into the electroporated cells, and
   wherein the piezoelectric pulse generator comprises:
      a piezoelectric crystal;
      a mechanism configured to strike a surface of the piezoelectric crystal effective to generate the one or more electrical pulses; and
      electrical connections configured to conduct the one or more electrical pulses to the microneedle electrodes.

2. The device of claim 1, further comprising (i) a base from which the array of microneedle electrodes extend, and (ii) a housing which is connected to the base and contains the piezoelectric pulse generator.

3. The device of claim 1, wherein the device further comprises the drug and is configured to release the drug to the biological tissue.

4. The device of claim 3, wherein the drug is coated onto the microneedle electrodes.

5. The device of claim 3, wherein:
   the drug is stored in one or more reservoirs in the device,
   at least a portion of the microneedle electrodes each includes a hollow bore or a groove on its surface, and
   the device includes one or more conduits which are in fluid communication with the one or more reservoirs and the hollow bores or grooves of the microneedle electrodes for passage of the drug.

6. The device of claim 1, wherein the drug is in the form of particles that contain the drug.

7. The device of claim 1, wherein the microneedle electrodes extend from one or more metal plates which are configured to conduct the electrical pulses from the piezoelectric pulse generator to the microneedle electrodes.

8. The device of claim 7, wherein a linear array of the microneedle electrodes extends from one edge of each of the metal plates.

9. The device of claim 7, wherein the one or more metal plates are two or more plates which are parallel to each other and spaced apart from one another.

10. The device of claim 1, wherein the microneedle electrodes extend from a single metal plate, and the array is a two-dimensional array.

11. The device of claim 1, wherein the microneedle electrodes extend from at least one non-electrically conductive plate and wherein electrical connections are provided between the microneedle electrodes and configured to conduct the one or more electrical pulses from the piezoelectric pulse generator to the microneedle electrodes.

12. The device of claim 11, wherein the electrical connections are located on a surface of the at least one non-electrically conductive plate.

13. The device of claim 11, wherein the electrical connections cross from a first side of the at least one non-electrically conductive plate to an opposed second side of the plate through holes in the at least one non-electrically conductive plate.

14. The device of claim 1, wherein the microneedle electrodes each comprise a non-electrically conductive core and a conductive electrode material the covers at least part of a surface of the microneedle core.

15. The device of claim 1, wherein the mechanism of the piezoelectric pulse generator comprises
   a spring-latch hammer.

16. The device of claim 1, wherein the piezoelectric crystal comprises lead zirconate titanate (PZT), silicon nitride, barium titanate, quartz, zinc oxide, or sodium tungstate.

17. The device of claim 15, further comprising (i) a toggle switch with a wedge controlling latch configured to release a hammer driven by decompression of a spring, and (ii) a metal pin disposed between the hammer and the piezoelectric crystal.

18. The device of claim 1, further comprises a casing for the piezoelectric crystal, wherein the electrical connections consist of a lower electrode and a side electrode, which extends from the casing.

19. The device of claim 18, further comprising a cartridge that contains the array of microneedle electrodes and includes a first receptacle for mating engagement with the lower electrode and a second receptacle for mating engagement with the side electrode, the first and second receptacles being in electrical communication with the microneedle electrodes.

20. The device of claim 1, wherein the array of microneedle electrodes is configured to be replaceable and disposable, and the piezoelectric pulse generator is configured to be reusable with a series of said arrays.

21. The device of claim 1, which is configured to produce one or more electrical pulses that have a peak voltage absolute value between 10 V and 10,000 V, between 50 V and 5,000 V, between 100 V and 1,000 V, or between 200 V and 500 V.

22. The device of claim 1, which is configured to produce one or more electrical pulses that have a ratio of absolute value of peak voltage to absolute value of peak-to-peak voltage between 0.1 and 10, between 0.3 and 5, or between 0.5 and 2.

23. The device of claim 1, which is configured to produce one or more electrical pulses that have a peak current absolute value between 1 A and 1,000 A, between 5 A and 500 A, between 10 A and 100 A, or between 20 A and 50 A.

24. The device of claim 1, which is configured to produce one or more electrical pulses that have a peak static voltage absolute value between 100 V and 35,000 V, between 1,000 V and 30,000 V, or between 15,000 V and 27,500 V.

25. The device of claim 1, which is configured to produce a nominal electric field strength between 100 V/cm and 30,000 V/cm, between 200 V/cm and 10,000 V/cm, between 300 V/cm and 5,000 V/cm, or between 500 V/cm and 3,500 V/cm.

26. The device of claim 1, which is configured to produce one or more electrical pulses that have an initial pulse length between 1 us and 1,000 us, between 3 us and 100 us, between 5 us and 50 us, or between 10 us and 30 us.

27. The device of claim 1, which is configured to produce one or more electrical pulses that have a ratio of initial pulse length to total pulse length between 1.5 and 100, between 2 and 50, or between 3 and 20.

28. The device of claim 1, wherein the microneedle electrodes have a spacing in the array between 0.1 mm and 10 mm, between 0.2 mm and 5 mm, between 0.3 mm and 2 mm, or between 0.5 mm and 1.5 mm.

29. A method of delivering a drug into or across a biological tissue, the method comprising:
positioning the device of claim 1 adjacent to a target tissue site in a biological tissue;
inserting the microneedle electrodes into the target tissue site; and
activating the device to deliver the one or more electrical pulses through the microneedle electrodes and into the target tissue site effective to electroporate cells at the target tissue site;
and delivering the drug into tissues of the target tissue site.

30. The device of claim 6, wherein the particles that contain the drug are drug-loaded lipid nanoparticles or drug-loaded polymeric nanoparticles.

* * * * *